United States Patent
Calandra et al.

(10) Patent No.: US 10,456,339 B2
(45) Date of Patent: Oct. 29, 2019

(54) ORGANIC HYDROPEROXIDE REDUCTION IN PERFUMERY RAW MATERIALS

(71) Applicant: FIRMENICH SA, Geneva (CH)

(72) Inventors: Michael J. Calandra, Plainsboro, NJ (US); Ying Wang, Plainsboro, NJ (US)

(73) Assignee: FIRMENICH SA, Geneva (CH)

( * ) Notice: Subject to any disclaimer, the term of this patent is extended or adjusted under 35 U.S.C. 154(b) by 0 days.

(21) Appl. No.: 16/162,839

(22) Filed: Oct. 17, 2018

(65) Prior Publication Data

US 2019/0046422 A1 Feb. 14, 2019

Related U.S. Application Data

(63) Continuation of application No. PCT/EP2018/061468, filed on May 4, 2018.

(60) Provisional application No. 62/502,156, filed on May 5, 2017.

(30) Foreign Application Priority Data

Jun. 16, 2017 (EP) .................................... 17176476

(51) Int. Cl.
  *A61K 8/22* (2006.01)
  *A61K 8/36* (2006.01)
  *A61Q 19/08* (2006.01)
  *A61Q 15/00* (2006.01)
  *A61Q 5/02* (2006.01)
  *A23D 9/007* (2006.01)

(52) U.S. Cl.
CPC .............. *A61K 8/22* (2013.01); *A23D 9/007* (2013.01); *A61K 8/36* (2013.01); *A61Q 5/02* (2013.01); *A61Q 15/00* (2013.01); *A61Q 19/08* (2013.01); *A23V 2002/00* (2013.01); *A23V 2200/15* (2013.01); *A23V 2250/052* (2013.01)

(58) Field of Classification Search
None
See application file for complete search history.

(56) References Cited

U.S. PATENT DOCUMENTS

| 3,689,277 | A | * | 9/1972 | Sfat et al. | ............... A23J 3/344 426/11 |
| 5,847,003 | A | | 12/1998 | Ptchelintsev et al. | |
| 2010/0166677 | A1 | | 7/2010 | Ptchelintsev | |
| 2011/0144142 | A1 | * | 6/2011 | Hu | ........................... A61K 8/36 514/275 |

FOREIGN PATENT DOCUMENTS

WO 2014035401 A1 3/2014

OTHER PUBLICATIONS

TGSC page for pyruvic acid (2006). Retrieved on Mar. 18, 2019 from <http://www.thegoodscentscompany.com/data/rw1034261.html>.*
"In the Mood for Oud?" article (2014) . Retreived from <https://www.townandcountrymag.com/style/beauty-products/a1935/oud-perfume/> on Mar. 18, 2019.*
International Search Report and Written Opinion for International Application No. PCT/EP2018/061468, dated Aug. 7, 2018.

* cited by examiner

*Primary Examiner* — Patricia Duffy
*Assistant Examiner* — Garen Gotfredson
(74) *Attorney, Agent, or Firm* — Armstrong Teasdale LLP

(57) ABSTRACT

The aspects presented herein provide methods and compositions for the reduction of the peroxide value of perfume ingredients, formulated perfumes, formulated body care products, formulated skin care products, formulated homecare products, essential oils, food raw materials, formulated food products, and natural extracts.

3 Claims, 16 Drawing Sheets

ORGANIC HYDROPEROXIDE REDUCTION IN PERFUMERY RAW MATERIALS

CROSS REFERENCE TO RELATED APPLICATIONS

The present application is a Continuation of International Patent Application Serial No. PCT/EP2018/061468, filed on May 4, 2018, and claims priority to U.S. Provisional Patent Application Ser. No. 62/502,156, filed on May 5, 2017, and European Patent Application Serial No. 17176476.4, filed on Jun. 16, 2017, the entire contents of which are hereby incorporated by reference in their entirety.

FIELD

The various aspects presented herein relate to methods and compositions for the reduction of the peroxide value of perfume ingredients, formulated perfumes, formulated body care products, formulated skin care products, formulated homecare products, essential oils, food raw materials, formulated food products, and natural extracts.

BACKGROUND

Many formulated perfumes, body care products, home care products, perfumery raw materials (such as, for example, essential oils, natural extracts, and synthetic ingredients), and food raw materials (such as, for example, fats and oils derived from animal or plant sources, and derivatives thereof, including monoglycerides, diglycerides, lecithins, phosphatidyl ethanolamines, or other phospholipids, and modified triglycerides) can undergo oxidation, resulting in the formation of chemical species including peroxides, organic hydroperoxides, peroxyhemiacetals.

The peroxide value (POV), defined as the amount of equivalents of oxidizing potential per 1 kilogram of material is an indication of the extent of the oxidation. The POV of formulated perfumes, body care products, and perfumery raw materials is, or may be subject to regulatory limits, due to skin sensitization issues, such as, for example, contact dermatitis. For example, an unacceptably high POV can result in a perfumery raw material failing quality control testing, and therefore being deemed unusable. In another example, an unacceptably high POV can result in a food raw material having an unpleasant rancid taste.

Consequently, there is a need to reduce the incidence of formulated perfumes, body care products and perfumery raw materials failing quality control testing, or, causing skin irritation, by reducing the POV in the formulated perfumes, body care products, home care products, cosmetic products, and perfumery raw materials. In addition, there is a need to reduce the occurrence of a rancid taste in food raw materials, by reducing the POV in the food raw materials.

SUMMARY

One aspect presented herein, provides a method for reducing the POV of a formulated perfume, body care product, cosmetic product, homecare product, perfumery raw material, flavored article, or food raw material, comprising the steps of: adding an α-oxocarboxylic acid to the formulated perfume, body care product, cosmetic product, homecare product, perfumery raw material, flavored article, or food raw material having a first POV level; and mixing the α-oxocarboxylic acid into the formulated perfume, body care product, cosmetic product, homecare product, perfumery raw material, flavored article, or food raw material for a time sufficient to reduce the first POV level to a pre-determined second lower level.

One aspect presented herein, provides a method for reducing, preventing, or ameliorating formulated perfume, body care product, homecare product, cosmetic product, or perfumery raw material-induced skin irritation of a subject in need thereof, comprising the steps of: (a) adding an α-oxocarboxylic acid to the formulated perfume, body care product, homecare product, cosmetic product, or perfumery raw material having a first POV level; and (b) mixing the α-oxocarboxylic acid into the formulated perfume, body care product, homecare product, cosmetic product, or perfumery raw material for a time sufficient to reduce the first POV level to a pre-determined second lower level, wherein the pre-determined second lower level is sufficient to reduce, prevent, or ameliorate the formulated perfume, body care product, homecare product, cosmetic product, or perfumery raw material-induced skin irritation of the subject.

In one aspect the perfumery raw material is selected from the group consisting of a synthetic ingredient, a natural product, an essential oil, and a natural extract.

In one aspect, the body care product is a skin cream.

In one aspect, the food raw material is selected from the group consisting of a fat, an oil, or a derivative thereof.

In one aspect, the derivative thereof is selected from the group consisting of a monoglyceride, a diglyceride, and a phospholipid.

In one aspect, the phospholipid is selected from the group consisting of a lecithin, a phosphatidyl ethanolamine, and a modified triglyceride.

In one aspect, the perfumery raw material is treated prior to the incorporation into a perfume.

In one aspect, the perfumery raw material is treated after the incorporation into a perfume.

In one aspect, the food raw material is treated prior to the incorporation into a flavored article.

In one aspect the food raw material is incorporated after the incorporation into a flavored article.

In one aspect, the concentration of the α-oxocarboxylic acid ranges from 0.001 to 10 weight percent, after the addition to the formulated perfume, body care product, cosmetic product, homecare product, perfumery raw material, flavored article, or food raw material.

In one aspect, the α-oxocarboxylic acid is selected from the group consisting of: pyruvic acid, 2-oxovaleric acid, phenylglyoxylic acid, 2-oxobutyric acid, 2-oxo-2-furanacetic acid, oxaloacetic acid, α-ketoglutaric acid, 2-oxopentandioate, indole-3-pyruvic acid, 2-thiopheneglyoxylic acid, trimethylpyruvic acid, 2-oxoadipic acid, 4-hydroxyphenylpyruvic acid, phenylpyruvic acid, 2-oxooctanoic acid, and mixtures thereof.

In one aspect, the perfumery raw material is citrus oil.

In one aspect, the food raw material is a cooking oil.

In one aspect, the pre-determined second lower level is between 5 and 20 mmol/L.

In one aspect, the pre-determined second lower level is between 0 and 6 mmol/L.

In one aspect, the method further comprises removing the excess α-oxocarboxylic acid from the formulated perfume, body care product, cosmetic product, homecare product, perfumery raw material, flavored article, or food raw material having the pre-determined second lower POV level.

In one aspect, the excess α-oxocarboxylic acid is removed from the formulated perfume, body care product, cosmetic product, homecare product, perfumery raw material, flavored article, or food raw material via a liquid-liquid extraction.

In one aspect, the method further comprises treating the formulated perfume, body care product, cosmetic product, homecare product, perfumery raw material, flavored article, or food raw material after removing the α-oxocarboxylic acid to reduce the acidity of the formulated perfume, body care product, cosmetic product, homecare product, perfumery raw material, flavored article, or food raw material.

In one aspect, the formulated perfume, body care product, cosmetic product, homecare product, perfumery raw material, flavored article, or food raw material is treated with a carbonate salt to reduce the acidity of the formulated perfume, body care product, cosmetic product, homecare product, perfumery raw material, flavored article, or food raw material.

One aspect presented herein, provides a composition comprising: (a) a formulated perfume, body care product, cosmetic product, homecare product, perfumery raw material, flavored article, or food raw material, and (b) an α-oxocarboxylic acid, wherein the α-oxocarboxylic acid is present in the composition in an amount sufficient to decrease the POV from a first level to a pre-determined second lower level.

One aspect presented herein, provides a composition comprising: (a) a formulated perfume, body care product, cosmetic product, homecare product, perfumery raw material, flavored article, or food raw material, and (b) an α-oxocarboxylic acid, wherein the α-oxocarboxylic acid is present in the composition in an amount sufficient to reduce, prevent, or ameliorate an increase in the POV of the formulated perfume, body care product, cosmetic product, homecare product, perfumery raw material, flavored article, or food raw material.

In one aspect, the α-oxocarboxylic acid is added to the formulated perfume, body care product, cosmetic product, homecare product, perfumery raw material, flavored article, or food raw material at a concentration ranging from 0.001 to 10 weight percent.

In one aspect, the perfumery raw material is citrus oil.

In one aspect, the α-oxocarboxylic acid is present in the composition in an amount sufficient to prevent the pre-determined second lower level from changing with time.

In one aspect, the concentration of the α-oxocarboxylic acid in the composition ranges from 0.001 to 10 weight percent.

In one aspect, the α-oxocarboxylic acid is added to the formulated perfume, body care product, cosmetic product, homecare product, perfumery raw material, flavored article, or food raw material as an inorganic salt.

In one aspect, the α-oxocarboxylic acid is present in the composition as an inorganic salt.

In one aspect the salt is an ammonium salt formed by reacting the α-oxocarboxylic acid with a compound selected from the group consisting of: 2-(dimethylamino)ethanol, N, N-dimethyldodecylamine, Tris[2 (2 (methoxyethoxy)ethyl] amine, and N-methyl diethanolamine.

In one aspect, the α-oxocarboxylic acid is added to the formulated perfume, body care product, cosmetic product, homecare product, perfumery raw material, flavored article, or food raw material as a salt of a mono or divalent cation.

In one aspect, the α-oxocarboxylic acid is present in the composition as a salt of a mono or divalent cation.

In one aspect, the α-oxocarboxylic acid is selected from the group consisting of: pyruvic acid, 2-oxovaleric acid, phenylglyoxylic acid, 2-oxobutyric acid, 2-oxo-2-furanacetic acid, oxaloacetic acid, α-ketoglutaric acid, 2-oxopentandioate, indole-3-pyruvic acid, 2-thiopheneglyoxylic acid, trimethylpyruvic acid, 2-oxoadipic acid, 4-hydroxyphenylpyruvic acid, phenylpyruvic acid, 2-oxooctanoic acid, and mixtures thereof.

DETAILED DESCRIPTION

Figure 1:
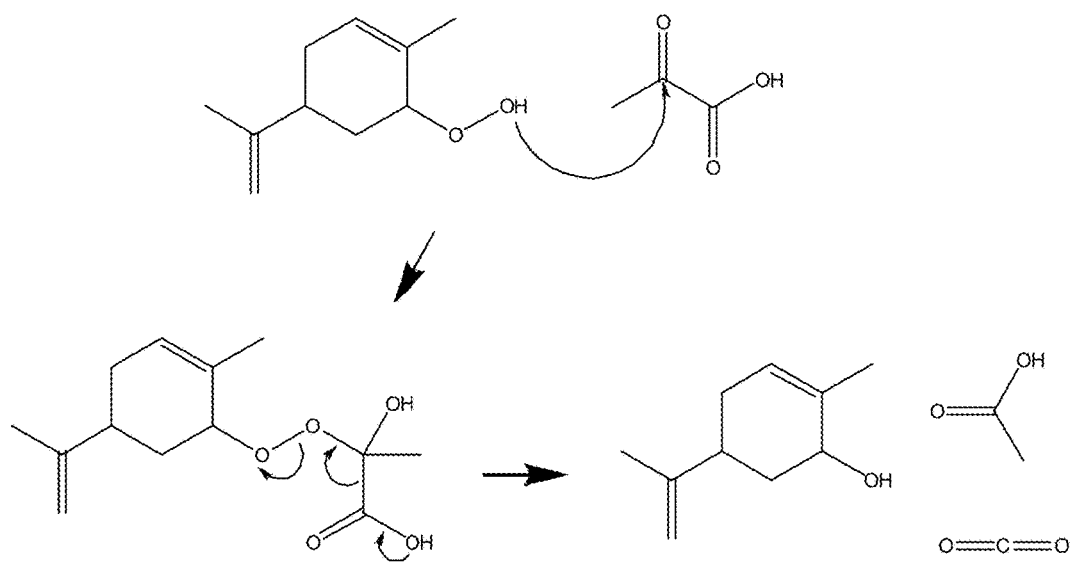
FIG. 1 shows an exemplar proposed reaction between an α-oxocarboxylic acid and an organic hydroperoxide according to certain aspects presented herein.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Many formulated perfumes, body care products, homecare products, perfumery raw materials (such as, for example, essential oils, natural extracts, and synthetic ingredients) can undergo oxidation, resulting in the formation of chemical species including peroxides, organic hydroperoxides, peroxyhemiacetals. In addition, many food raw materials, such as, for example, fats oils, or derivatives thereof, are known to undergo an autoxidation process that results in the formation of the intermediate chemical species glyceride hydroperoxides. The glyceride hydroperoxides may further degrade into aldehydes and ketones. Without intending to be limited to any particular theory the autoxidation process may result in an unpleasant and unpalatable rancidity of the food raw material.

The peroxide value (POV), defined as the amount of equivalents of oxidizing potential per 1 kilogram of material is an indication of the extent of the oxidation. The POV of formulated perfumes, body care products, homecare products, cosmetic products, and perfumery raw materials is subject to regulatory limits due to skin sensitization issues, such as, for example, contact dermatitis. For example, an unacceptably high POV can result in a perfumery raw material failing quality control testing, and therefore being deemed unusable. In another example an unacceptably high POV can result in a food raw material, or a formulated food product (also referred to herein as a flavored article) having a rancid taste.

Skin exposure may be the result of an incidental exposure (such as, for example, of a hard surface cleaner or a hand dishwashing soap when the user does not wear a pair of gloves when using the product). Alternatively, skin exposure may be the result of a long-term, or intentional exposure (such as, for example, of a shampoo, or skin moisturizer).

As used herein, the term "peroxide value" or "POV" refers to the amount of equivalents of oxidizing potential per 1 kilogram of material. Without intending to be limited to any particular theory, the POV of a material is determined analytically. The term "POV" does not refer to a chemical compound or group of compounds, but is often used loosely and interchangeably with the products of autoxidation within a sample that cause a response during a POV test. These autoxidation products differ depending upon the particular material being tested. Many classes of chemical compounds will produce a response during a POV test, including but not limited to organic and inorganic hydroperoxides, organic and inorganic peroxides, peroxyhemiacetals, peroxyhemiketals, and hydrogen peroxide itself.

By way of illustration, one POV test is an iodometric oxidation-reduction titration. All POV-responsive compounds share the property that they are capable of oxidizing the iodide ion to molecular iodine within the time period specified for the test; in fact, the iodide oxidation reaction is the basis for the test. Thus, "POV" is a numerical value that represents the molar sum total of the all the iodide-oxidizing species in a particular sample.

By way of illustration, limonene and linalool are unsaturated terpenes commonly found as major components in many essential oils. Both limonene and linalool are easily oxidized by atmospheric oxygen to form hydroperoxides. The hydroperoxides of limonene and linalool are known to be sensitizers capable of causing contact dermatitis. Consequently, limonene, and natural products containing limonene may only be used as perfumery raw materials when the recommended organic hydroperoxide level is below 20 mmol/L (or 10 mEq/L). Similarly, essential oils and isolates derived from the Pinacea family, including *Pinus* and *Abies* genera may only be used as perfumery raw materials when the recommended organic hydroperoxide level is below 10 mmol/L (or 5 mEQ/L).

By way of another illustration, fats oils, or derivatives thereof, are known to undergo an autoxidation process that leads to unpleasant and unpalatable rancidity. Without intending to be limited to any particular theory, glyceride hydroperoxides are an intermediate chemical species in the autoxidation process, which further degrade into aldehydes and ketones that produce the rancid aroma.

The POV of a perfumery raw material may be determined by any method readily selectable by one of ordinary skill in the art. Non limiting examples include, iodometric titration, high-performance liquid chromatography, and the like.

An example of a method for determining the POV of a perfumery raw material is disclosed in Calandra et al., Flavour and Fragr. J. (2015), 30, p 121-130.

Perfumery raw materials include, but are not limited to essential oils, natural extracts, and synthetic ingredients.

The POV of a formulated perfume, body care product, cosmetic product, homecare product, perfumery raw material, flavored article, or food raw material may be determined by any method readily selectable by one of ordinary skill in the art. No limiting examples include, iodometric titration, high-performance liquid chromatography, and the like.

An example of a method for determining the POV of a formulated perfume is disclosed in Calandra et al., Flavour and Fragr. J. (2015), 30, p 121-130.

The POV of a formulated body care product may be determined by any method readily selectable by one of ordinary skill in the art. Non-limiting examples include iodometric titration, high-performance liquid chromatography, and the like.

An example of a method for determining the POV of a formulated body care product is disclosed in Calandra et al., Flavour and Fragr. J. (2015), 30, p 121-130.

Without intending to be limited to any particular theory, the POV of the formulated perfume, body care product, cosmetic product, homecare product, perfumery raw material, flavored article, or food raw material is reduced by treating the formulated perfume, body care product, cosmetic product, homecare product, perfumery raw material, flavored article, or food raw material with an α-oxocarboxylic acid. The α-oxocarboxylic acid reacts with the organic hydroperoxide via oxidative decarboxylation, thereby consuming the organic hydroperoxide, reducing the organic hydroperoxide's oxidative potential. The resulting reaction results in the oxidation of the α-oxocarboxylic acid to carbon dioxide and the corresponding carboxylic acid containing one less carbon atom, and the reduction of the organic hydroperoxide to its corresponding organic alcohol. An exemplar proposed reaction, using pyruvic acid as the α-oxocarboxylic acid and limonene-hydroperoxide as the organic hydroperoxide is depicted in FIG. 1.

Accordingly, one aspect presented herein, provides a method for reducing the POV of a perfumery raw material, comprising the steps of: adding an α-oxocarboxylic acid to the perfumery raw material having a first POV level; and mixing the α-oxocarboxylic acid into the perfumery raw material for a time sufficient to reduce the first POV level to a pre-determined second lower level.

An alternate aspect presented herein, provides a method for reducing, preventing, or ameliorating perfumery raw material-induced skin irritation of a subject in need thereof, comprising the steps of: (a) adding an α-oxocarboxylic acid to the perfumery raw material having a first POV level; and (b) mixing the α-oxocarboxylic acid into the perfumery raw material for a time sufficient to reduce the first POV level to a pre-determined second lower level, wherein the pre-determined second lower level is sufficient to reduce, prevent, or ameliorate the perfumery raw material-induced skin irritation of the subject.

An alternate aspect presented herein, provides a method for reducing the POV of a formulated perfume, comprising the steps of: adding an α-oxocarboxylic acid to the formulated perfume having a first POV level; and mixing the α-oxocarboxylic acid into the formulated perfume for a time sufficient to reduce the first POV level to a pre-determined second lower level.

An alternate aspect presented herein, provides a method for reducing, preventing, or ameliorating formulated perfume-induced skin irritation of a subject in need thereof, comprising the steps of: (a) adding an α-oxocarboxylic acid to the formulated perfume having a first POV level; and (b) mixing the α-oxocarboxylic acid into the formulated perfume for a time sufficient to reduce the first POV level to a pre-determined second lower level, wherein the pre-determined second lower level is sufficient to reduce, prevent, or ameliorate the formulated perfume-induced skin irritation of the subject.

An alternate aspect presented herein, provides a method for reducing the POV of a formulated personal care product, comprising the steps of: adding an α-oxocarboxylic acid to the formulated personal care product having a first POV level; and mixing the α-oxocarboxylic acid into the formulated personal care product for a time sufficient to reduce the first POV level to a pre-determined second lower level.

An alternate aspect presented herein, provides a method for reducing, preventing, or ameliorating formulated personal care product-induced skin irritation of a subject in need thereof, comprising the steps of: (a) adding an α-oxocarboxylic acid to the formulated personal care product having a first POV level; and (b) mixing the α-oxocarboxylic acid into the formulated personal care product for a time sufficient to reduce the first POV level to a pre-determined second lower level, wherein the pre-determined second lower level is sufficient to reduce, prevent, or ameliorate the formulated personal care product-induced skin irritation of the subject.

An alternate aspect presented herein, provides a method for reducing the POV of a formulated cosmetic product, comprising the steps of: adding an α-oxocarboxylic acid to the formulated cosmetic product having a first POV level; and mixing the α-oxocarboxylic acid into the formulated cosmetic product for a time sufficient to reduce the first POV level to a pre-determined second lower level.

An alternate aspect presented herein, provides a method for reducing, preventing, or ameliorating formulated cosmetic product-induced skin irritation of a subject in need thereof, comprising the steps of: (a) adding an α-oxocarboxylic acid to the formulated cosmetic product having a first POV level; and (b) mixing the α-oxocarboxylic acid into the formulated cosmetic product for a time sufficient to reduce the first POV level to a pre-determined second lower level, wherein the pre-determined second lower level is sufficient to reduce, prevent, or ameliorate the formulated cosmetic product-induced skin irritation of the subject.

An alternate aspect presented herein, provides a method for reducing the POV of a formulated homecare product, comprising the steps of: adding an α-oxocarboxylic acid to the formulated homecare product having a first POV level; and mixing the α-oxocarboxylic acid into the formulated homecare product for a time sufficient to reduce the first POV level to a pre-determined second lower level.

An alternate aspect presented herein, provides a method for reducing, preventing, or ameliorating formulated homecare product-induced skin irritation of a subject in need thereof, comprising the steps of: (a) adding an α-oxocarboxylic acid to the formulated homecare product having a first POV level; and (b) mixing the α-oxocarboxylic acid into the formulated homecare product for a time sufficient to reduce the first POV level to a pre-determined second lower level, wherein the pre-determined second lower level is sufficient to reduce, prevent, or ameliorate the formulated homecare product-induced skin irritation of the subject.

In one aspect, the method is performed at room temperature. In one aspect, the method is performed at a temperature ranging from −20 degrees Celsius to 78 degrees Celsius.

In one aspect the perfumery raw material is selected from the group consisting of a synthetic ingredient, a natural product, an essential oil, and a natural extract.

In one aspect, the perfumery raw material is citrus oil.

In one aspect, the perfumery raw material is treated prior to the incorporation into a perfume.

In one aspect, the perfumery raw material is treated after the incorporation into a perfume.

In one aspect, the pre-determined second lower level is between 5 and 20 mmol/L. In an alternate aspect, the pre-determined second lower level is between 5 and 19 mmol/L. In an alternate aspect, the pre-determined second lower level is between 5 and 18 mmol/L. In an alternate aspect, the pre-determined second lower level is between 5 and 17 mmol/L. In an alternate aspect, the pre-determined second lower level is between 5 and 16 mmol/L. In an alternate aspect, the pre-determined second lower level is between 5 and 15 mmol/L. In an alternate aspect, the pre-determined second lower level is between 5 and 14 mmol/L. In an alternate aspect, the pre-determined second lower level is between 5 and 13 mmol/L. In an alternate aspect, the pre-determined second lower level is between 5 and 12 mmol/L. In an alternate aspect, the pre-determined second lower level is between 5 and 11 mmol/L. In an alternate aspect, the pre-determined second lower level is between 5 and 10 mmol/L. In an alternate aspect, the pre-determined second lower level is between 5 and 9 mmol/L. In an alternate aspect, the pre-determined second lower level is between 5 and 8 mmol/L. In an alternate aspect, the pre-determined second lower level is between 5 and 7 mmol/L. In an alternate aspect, the pre-determined second lower level is between 5 and 6 mmol/L.

In one aspect, the pre-determined second lower level is between 6 and 20 mmol/L. In an alternate aspect, the pre-determined second lower level is between 7 and 20 mmol/L. In an alternate aspect, the pre-determined second lower level is between 8 and 20 mmol/L. In an alternate aspect, the pre-determined second lower level is between 9 and 20 mmol/L. In an alternate aspect, the pre-determined second lower level is between 10 and 20 mmol/L. In an alternate aspect, the pre-determined second lower level is between 11 and 20 mmol/L. In an alternate aspect, the pre-determined second lower level is between 12 and 20 mmol/L. In an alternate aspect, the pre-determined second lower level is between 13 and 20 mmol/L. In an alternate aspect, the pre-determined second lower level is between 14 and 20 mmol/L. In an alternate aspect, the pre-determined second lower level is between 15 and 20 mmol/L. In an alternate aspect, the pre-determined second lower level is between 16 and 20 mmol/L. In an alternate aspect, the pre-determined second lower level is between 17 and 20 mmol/L. In an alternate aspect, the pre-determined second lower level is between 18 and 20 mmol/L. In an alternate aspect, the pre-determined second lower level is between 19 and 20 mmol/L.

In one aspect, the pre-determined second lower level is 20 mmol/L. In an alternate aspect, the pre-determined second lower level is 19 mmol/L. In an alternate aspect, the pre-determined second lower level is 18 mmol/L. In an alternate aspect, the pre-determined second lower level is 17 mmol/L. In an alternate aspect, the pre-determined second lower level is 16 mmol/L. In an alternate aspect, the pre-determined second lower level is 15 mmol/L. In an alternate aspect, the pre-determined second lower level is 14 mmol/L. In an alternate aspect, the pre-determined second lower level is 13 mmol/L. In an alternate aspect, the pre-determined second lower level is 12 mmol/L. In an alternate aspect, the pre-determined second lower level is 11 mmol/L. In an alternate aspect, the pre-determined second lower level is 10 mmol/L. In an alternate aspect, the pre-determined second lower level is 9 mmol/L. In an alternate aspect, the pre-determined second lower level is 8 mmol/L. In an alternate aspect, the pre-determined second lower level is 7 mmol/L. In an alternate aspect, the pre-determined second lower level is 6 mmol/L. In an alternate aspect, the pre-determined second lower level is 5 mmol/L. In an alternate aspect, the pre-determined second lower level is 4 mmol/L. In an alternate aspect, the pre-determined second lower level is 3 mmol/L. In an alternate aspect, the pre-determined second lower level is 2 mmol/L. In an alternate aspect, the pre-determined second lower level is 1 mmol/L. In an alternate aspect, the pre-determined second lower level is less than 1 mmol/L.

In one aspect, the pre-determined second lower level is a 10% reduction in the POV. In an alternate aspect, the pre-determined second lower level is a 20, or 30, or 40, or 50, or 60, or 70, or 80, or 90, or 100% reduction in the POV.

An alternate aspect presented herein, provides a method for reducing the POV of a food raw material, comprising the steps of: adding an α-oxocarboxylic acid to the food raw material having a first POV level; and mixing the α-oxocarboxylic acid into the food raw material for a time sufficient to reduce the first POV level to a pre-determined second lower level.

An alternate aspect presented herein, provides a method for reducing the POV of a flavored article, comprising the steps of: adding an α-oxocarboxylic acid to the flavored article having a first POV level; and mixing the α-oxocarboxylic acid into the flavored article for a time sufficient to reduce the first POV level to a pre-determined second lower level.

Without intending to be limited to any particular theory, reducing the POV of a flavored article or a food raw material, prevents, reduces, or inhibits the formation of the intermediate glyceride hydroperoxides in the flavored article or the food raw material. Reducing, or inhibiting, or preventing the formation of the intermediate glyceride hydroperoxides in the flavored article or the food raw material may prevent, reduce, or delay the development of rancidity in the flavored article or the food raw material.

A flavored article includes, for example, a food product (e.g., a beverage), a sweetener such as a natural sweetener or an artificial sweetener, a pharmaceutical composition, a dietary supplement, a nutraceutical, a dental hygienic composition and a cosmetic product. The flavored article may further contain at least one flavoring.

In some aspects, the at least one flavoring may further modify the taste profile or taste attributes of the flavored article.

In some aspects, the flavored article is a food product including, for example, but not limited to, fruits, vegetables, juices, meat products such as ham, bacon and sausage, egg products, fruit concentrates, gelatins and gelatin-like products such as jams, jellies, preserves and the like, milk products such as ice cream, sour cream and sherbet, icings, syrups including molasses, corn, wheat, rye, soybean, oat, rice and barley products, nut meats and nut products, cakes, cookies, confectioneries such as candies, gums, fruit flavored drops, and chocolates, chewing gums, mints, creams, pies and breads.

In some aspects, the food product is a beverage including, for example, but not limited to, juices, juice containing beverages, coffee, tea, carbonated soft drinks, such as COKE and PEPSI, non-carbonated soft drinks and other fruit drinks, sports drinks such as GATORADE and alcoholic beverages such as beers, wines and liquors.

A flavored article may also include prepared packaged products, such as granulated flavor mixes, which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like.

A flavored article may also include diet or low-calorie food and beverages containing little or no sucrose. Flavored articles may also include condiments such as herbs, spices and seasonings, flavor enhancers (e.g., monosodium glutamate), dietetic sweeteners and liquid sweeteners.

In some aspects, the flavored article is a pharmaceutical composition, a dietary supplement, a nutraceutical, a dental hygienic composition or a cosmetic product.

Dental hygiene compositions are known in the art and include, for example, but not limited to, a toothpaste, a mouthwash, a plaque rinse, a dental floss, a dental pain reliever (such as ANBESOL) and the like. In some aspects, the dental hygiene composition includes one natural sweetener. In some aspects, the dental hygiene composition includes more than one natural sweetener. In some aspects, the dental hygiene composition includes sucrose and corn syrup, or sucrose and aspartame.

In some aspects, a cosmetic product includes, for example, but not limited to, a face cream, a lipstick, a lip gloss and the like. Other suitable cosmetic products of use in this disclosure include a lip balm, such as CHAPSTICK or BURT'S BEESWAX Lip Balm.

An alternate aspect presented herein, provides a method for increasing the shelf life of a food raw material, comprising the steps of: adding an α-oxocarboxylic acid to the food raw material having a first POV level; and mixing the α-oxocarboxylic acid into the food raw material for a time sufficient to reduce the first POV level to a pre-determined second lower level. Without intending to be limited to any particular theory, the reduction of the first POV level to a pre-determined second lower level prevents, reduces, or inhibits the formation of the intermediate glyceride hydroperoxides in the food raw material, resulting in the prevention, reduction, inhibition of the development of rancidity in the food raw material.

Without intending to be limited to any particular theory, the food raw material may be employed as a solvent for a flavoring ingredient, or, alternatively, the food raw material itself may be a flavoring ingredient.

An alternate aspect presented herein, provides a method for increasing the shelf life of flavored article, comprising the steps of: adding an α-oxocarboxylic acid to the flavored article having a first POV level; and mixing the α-oxocarboxylic acid into the flavored article for a time sufficient to reduce the first POV level to a pre-determined second lower level. Without intending to be limited to any particular theory, the reduction of the first POV level to a pre-determined second lower level prevents, reduces, or inhibits the formation of the intermediate glyceride hydroperoxides in the flavored article, resulting in the prevention, reduction, inhibition of the development of rancidity in the flavored article.

In one aspect, the food raw material is selected from the group consisting of a fat, an oil, or a derivative thereof. In one aspect, the derivative thereof is selected from the group consisting of a monoglyceride, a diglyceride, and a phospholipid. In one aspect, the phospholipid is selected from the group consisting of a lecithin, a phosphatidyl ethanolamine, and a modified triglyceride.

In one aspect, the food raw material is treated prior to the incorporation into a flavored article. In an alternate aspect the food raw material is incorporated after the incorporation into a flavored article.

In one aspect, the food raw material is a cooking oil. Examples of cooking oils suitable for treatment according to the aspects described herein include, but are not limited to: olive oil, palm oil, soybean oil, canola oil (rapeseed oil), corn oil, peanut oil, other vegetable oils, and animal-based oils, such as, for example, butter or lard.

In one aspect, the method is performed at room temperature. In one aspect, the method is performed at a temperature ranging from −20 degrees Celsius to 78 degrees Celsius.

In one aspect, the pre-determined second lower level is between 0 and 6 mmol/L. In an alternate aspect, the pre-determined second lower level is between 0 and 5 mmol/L. In an alternate aspect, the pre-determined second lower level is between 0 and 4 mmol/L. In an alternate aspect, the pre-determined second lower level is between 0 and 3 mmol/L. In an alternate aspect, the pre-determined second lower level is between 0 and 2 mmol/L. In an alternate aspect, the pre-determined second lower level is between 0 and 1 mmol/L.

In one aspect, the pre-determined second lower level is between 1 and 6 mmol/L. In an alternate aspect, the pre-determined second lower level is between 2 and 5 mmol/L. In an alternate aspect, the pre-determined second lower level is between 3 and 5 mmol/L. In an alternate aspect, the pre-determined second lower level is between 4 and 5 mmol/L.

In one aspect, the pre-determined second lower level is 5 mmol/L. In an alternate aspect, the pre-determined second lower level is 4 mmol/L. In an alternate aspect, the pre-determined second lower level is 3 mmol/L. In an alternate aspect, the pre-determined second lower level is 2 mmol/L. In an alternate aspect, the pre-determined second lower level is 1 mmol/L. In an alternate aspect, the pre-determined second lower level is 0.9 mmol/L. In an alternate aspect, the pre-determined second lower level is 0.8 mmol/L. In an alternate aspect, the pre-determined second lower level is 0.7 mmol/L. In an alternate aspect, the pre-determined second lower level is 0.6 mmol/L. In an alternate aspect, the pre-determined second lower level is 0.5 mmol/L. In an alternate aspect, the pre-determined second lower level is 0.4 mmol/L. In an alternate aspect, the pre-determined second lower level is 0.3 mmol/L. In an alternate aspect, the pre-determined second lower level is 0.2 mmol/L. In an alternate aspect, the pre-determined second lower level is 0.1 mmol/L. In an alternate aspect, the pre-determined second lower level is 0 mmol/L.

In one aspect, the pre-determined second lower level is a 10% reduction in the POV. In an alternate aspect, the pre-determined second lower level is a 20, or 30, or 40, or 50, or 60, or 70, or 80, or 90, or 100% reduction in the POV.

In one aspect, the α-oxocarboxylic acid has FEMA-GRAS status. In one aspect, the α-oxocarboxylic acid is selected from the group consisting of: pyruvic acid, 2-oxovaleric acid, phenylglyoxylic acid, 2-oxobutyric acid, 2-oxo-2-furanacetic acid, oxaloacetic acid, α-ketoglutaric acid, 2-oxopentandioate, indole-3-pyruvic acid, 2-thiopheneglyoxylic acid, trimethylpyruvic acid, 2-oxoadipic acid, 4-hydroxyphenylpyruvic acid, phenylpyruvic acid, 2-oxooctanoic acid, and mixtures thereof.

In some aspects, the at least one α-oxocarboxylic acid is added to the formulated perfume, body care product, cosmetic product, homecare product, perfumery raw material, flavored article, or food raw material as a salt. The salt may be formed by reacting the at least one α-oxocarboxylic acid with an organic base.

In the aspects where the at least one α-oxocarboxylic acid is a mono-acid, the resultant salt may be a mono-salt. In the aspects where the at least one α-oxocarboxylic acid is a di-acid, the resultant salt may be a mono-salt, or a di-salt.

Examples of suitable organic bases include, but are not limited to the organic bases described in Examples 7-11 below, polymeric amines, polyetylamines, and the like.

Alternatively, the salt may be formed by reacting the at least one α-oxocarboxylic acid with a cation selected from the group consisting of: $Na^+$, $K^+$, $Mg^{2+}$, and $Ca^{2+}$.

An example of an ammonium salt includes the ammonium salt formed by reacting the at least one α-oxocarboxylic acid with N-methyl diethanolamine.

In some aspects, the molar ratio of the at least one α-oxocarboxylic acid to N-methyl diethanolamine may be 1:2, or 1:1, or 2:1.

In some aspects, the ammonium salt of the at least one α-oxocarboxylic acid possesses surfactant properties. Without intending to be limited to any particular theory, surfactant properties typically arise in molecules that contain an ionic and/or highly polar functional groups in the molecule, along with one or more spatially separated, long hydrophobic section(s). If a hydrophobic moiety, such as an alkyl group with a sufficient number of carbons (for example, C-8 to C-24) is bound to the ammonium salt of the at least one α-oxocarboxylic acid, the resulting molecule may demonstrate surfactant properties.

Without intending to be limited to any particular theory, an ammonium salt of the at least one α-oxocarboxylic acid possessing surfactant properties, or that is ionic and highly polar may be useful in a variety of home care and body care consumer products that come in contact with the user's skin during use.

Examples of ammonium salts of the at least one α-oxocarboxylic acid having surfactant properties include, but are not limited to: the diammonium salt made from alpha-ketoglutaric acid and N, N-dimethyldodecylamine in a 1:2 molar ratio, and the monoammonium salt made from alpha-ketoglutaric acid and N, N-dimethyldodecylamine in a 1:1 molar ratio.

In some aspects, the ammonium salt of the at least one α-oxocarboxylic acid possesses emollient properties. Without intending to be limited to any particular theory, emollient properties typically arise in molecules that are predominately hydrophobic and inert with low melting points (relative to body temperature) can act as emollients. Useful emollients have oily or grease-like physical properties, and act as softening agents and/or moisture barriers when applied to the skin. While the ammonium salt of the at least one α-oxocarboxylic acid listed above are ionic and highly polar in character, if a sufficient quantity of hydrophobic moieties can be incorporated into an ammonium salt of the at least one α-oxocarboxylic acid, the resulting molecule may display emollient characteristics.

One approach is to use an amine that has three long, hydrophobic or oily substituents as the base component of the ammonium salt of the at least one α-oxocarboxylic acid. Such a molecule may have hydroperoxide consuming/POV lowering qualities along with emollient properties, and therefore provide additional benefits to the user. These would be useful in a variety of body care consumer products that are placed onto the skin during use and left on for extended periods for purposes of moisturizing, protecting, or softening the user's skin.

Examples of ammonium salts of the at least one α-oxocarboxylic acid having emollient properties include, but are not limited to: the diammonium salt made from alpha-ketoglutaric acid and Tris[2 (2 (methoxyethoxy)ethyl]amine in a 1:2 molar ratio.

In some aspects, the at least one α-oxocarboxylic acid may be reacted with N-methyl diethanolamine by dissolving the at least one α-oxocarboxylic acid in a solvent, such as, for example, acetone, and adding N-methyl diethanolamine to the solution. The resultant opaque, white emulsion may then be vortexed, during which time a second phase may coalesce. The mixture may then be placed in a freezer for at least 30 minutes, causing the bottom phase to thicken to a waxy solid. While still cold, the top layer may then be easily removed via decantation and discarded. Residual acetone may be removed from the bottom product layer via a stream of nitrogen followed by treatment in a vacuum oven at room temperature, thereby resulting in a faint yellow, highly viscous oil at room temperature comprising the diammonium salt.

Other compounds suitable to form an ammonium salt via reaction with the at least one α-oxocarboxylic acid include, 2-(dimethylamino)ethanol, and N, N-dimethyldodecylamine.

In one aspect the salt is an ammonium salt formed by reacting the α-oxocarboxylic acid with a compound selected from the group consisting of: 2-(dimethylamino)ethanol, N, N-dimethyldodecylamine, Tris[2 (2 (methoxyethoxy)ethyl] amine, and N-methyl diethanolamine.

Without intending to be limited to any particular theory, the ammonium salt of the at least one α-oxocarboxylic acid may prevent acid-catalyzed chemical reactions from occurring that can harm and/or degrade the treated formulated perfume, body care product, cosmetic product, homecare product, perfumery raw material, flavored article, or food raw material. Alternatively, the ammonium salt of the at least one α-oxocarboxylic acid may improve the solubility of the at least one α-oxocarboxylic acid. Alternatively, the ammonium salt of the at least one α-oxocarboxylic acid may provide an emulsifying effect.

Without intending to be limited to any particular theory, a salt of the at least one α-oxocarboxylic acid, when added to an aqueous system comprising the formulated perfume, body care product, cosmetic product, homecare product, perfumery raw material, flavored article, or food raw material may be an emulsifier. Such a composition may be useful for salad dressings, marinades, sauces, and the like.

In one aspect, the ammonium salt of the at least one α-oxocarboxylic acid may be further combined with at least one other agent. In one aspect, the at least one other agent is chitosan.

In one aspect, alpha-ketoglutaric acid is added to a mixture of palmitic acid and chitosan. Such a composition may be an emulsifier for the food oil in an aqueous system, and may be useful for salad dressings, marinades, sauces, and the like.

In one aspect, the time sufficient to reduce the POV to a pre-determined second lower level is 30, or 29, or 28, or 27, or 26, or 25, or 24, or 23, or 22, or 21, or 20, or 19, or 18, or 17, or 16, or 15, or 14, or 13, or 12, or 11, or 10, or 9, or 8, or 7, or 6, or 5, or 4, or 3, or 2, or 1 day(s).

In one aspect, the time sufficient to reduce the POV to a pre-determined second lower level is greater than 24 hours. In one aspect, the time sufficient to reduce the POV to a pre-determined second lower level is 48, or 47, or 46, or 45, or 44, or 43, or 42, or 41, or 40, or 39, or 38, or 37, or 36, or 35, or 34, or 33, or 32, or 31, or 30, or 29, or 28, or 27, or 26, or 25, or 24, or 23, or 22, or 21, or 20, or 19, or 18, or 17, or 16, or 15, or 14, or 13, or 12, or 11, or 10, or 9, or 8, or 7, or 6, or 5, or 4, or 3, or 2, or 1 hour(s).

In one aspect, the time sufficient to reduce the POV to a pre-determined second lower level is 60 minutes or less. In one aspect, the time sufficient to reduce the POV to a pre-determined second lower level is 60, or 50, or 40, or 30, or 20, or 10, or 9, or 8, or 7, or 6, or 5, or 4, or 3, or 2, or 1 minute.

Without intending to be limited to any particular theory, the amount of the α-oxocarboxylic acid and/or the rate at which the α-oxocarboxylic is added to the formulated perfume, body care product, cosmetic product, homecare product, perfumery raw material, flavored article, or food raw material is controlled to ensure that an excess of the α-oxocarboxylic does not accumulate. An excess accumulation of the α-oxocarboxylic may result, for example, in acid-catalyzed damage to the formulated perfume, body care product, cosmetic product, homecare product, perfumery raw material, flavored article, or food raw material.

The amount of the α-oxocarboxylic acid that is added to the formulated perfume, body care product, perfumery raw material, flavored article, or food raw material is dependent on several factors, including, but not limited to, the stability of the α-oxocarboxylic acid in solution, the solubility of the α-oxocarboxylic acid in the formulated perfume, body care product, perfumery raw material, flavored article, or food raw material, the pKa of the α-oxocarboxylic acid, the rate of reduction of the POV, the effect the α-oxocarboxylic acid has on the olfactive properties and/or taste of the formulated perfume, body care product, perfumery raw material, flavored article, or food raw material.

By way of illustration, pyruvic acid, phenylpyruvic acid, and 2-oxovaleric acid possess strong aromas are used as FEMA-GRAS flavoring components. In these aspects, the intrinsic odors of the α-oxocarboxylic acid may alter, or be incompatible with the organoleptic quality of a formulated perfume, for example.

An alternative to using an odorless α-oxocarboxylic acid in the aspects described herein is the use of an α-oxocarboxylic acid that is compatible with the fragrance of the perfume, and when consumed by reaction with hydroperoxides, that also liberates a carboxylic acid that is compatible with the fragrance. By way of illustration, indole-3-pyruvic acid nay be used to reduce the POV of a fragrance that has an indolic character (i.e. contains perceivable amounts of indole and/or skatole).

Examples of an α-oxocarboxylic acid that is odorless include α-ketoglutaric acid. Without intending to be limited to any particular theory, an odorless α-oxocarboxylic acid may reduce the POV of a formulated perfume, body care product, cosmetic product, homecare product, perfumery raw material, flavored article, or food raw material with a lower impact on the organoleptic properties of the formulated perfume, body care product, cosmetic product, homecare product, perfumery raw material, flavored article, or food raw material, compared to an α-oxocarboxylic acid that has an odor.

The solubility of the α-oxocarboxylic acid may change if the composition comprising the α-oxocarboxylic acid is formulated differently. Using α-ketoglutaric acid as an example, the solubility of the α-oxocarboxylic acid may be low in a perfume raw material such citrus oil. However, the solubility of the α-oxocarboxylic acid may increase, if the perfume raw material is added to a hydroalcoholic perfume base (a solution comprising from 80% to 90% ethanol in water). In these aspects, if the α-oxocarboxylic acid is a strong acid, the amount of the α-oxocarboxylic acid in solution in the hydroalcoholic perfume base may have to be limited, to prevent alterations of the organoleptic properties on the perfume raw materials or the formulated perfume due to the acid-catalyzed degradation of the perfume raw material.

Examples of aspects where the α-oxocarboxylic acid may be unstable in solution include oxaloacetic acid, which is unstable in aqueous solution. In these aspects, the oxaloacetic acid breaks down to pyruvic acid, and carbon dioxide. In these aspects, reduction of the POV of the formulated perfume, body care product, perfumery raw material, flavored article, or food raw material may be via the oxaloacetic acid, the pyruvic acid, or any combination thereof.

In some aspects, the solubility of the α-oxocarboxylic acid in the formulated perfume, body care product, cosmetic product, homecare product, perfumery raw material, flavored article, or food raw material is low. By way of illustration, at the lower limit of solubility, the α-oxocarboxylic acid may be practically insoluble in the formulated perfume, body care product, cosmetic product, homecare product, perfumery raw material, flavored article, or food raw material. In contrast, at the upper limit of solubility, the α-oxocarboxylic acid may be fully miscible in the formulated perfume, body care product, cosmetic product, homecare product, perfumery raw material, flavored article, or food raw material.

Examples of aspects where the solubility of the α-oxocarboxylic acid in formulated perfume, body care product, cosmetic product, homecare product, perfumery raw material, flavored article, or food raw material is low include, but are not limited to pyruvic acid in citrus oil. In these aspects, the α-oxocarboxylic acid may be added at a concentration in excess of the solubility, thus forming a two-phase system, wherein one phase consists of the α-oxocarboxylic acid. Without intending to be limited to any particular theory, components of the formulated perfume, body care product, cosmetic product, homecare product, perfumery raw material, flavored article, or food raw material may partition into the phase consisting of the α-oxocarboxylic acid. Exposure of the components of the formulated perfume, body care product, cosmetic product, homecare product, perfumery raw material, flavored article, or food raw material to the phase consisting of the α-oxocarboxylic acid may result in chemical changes/damage to acid-sensitive compounds in the formulated perfume, body care product, cosmetic product, homecare product, perfumery raw material, flavored article, or food raw material.

By way of illustration, essential oils are composed largely of terpene compounds. As a class, terpenes are generally subject to acid-catalyzed rearrangements. Consequently, exposure of the components of the formulated perfume, body care product, cosmetic product, homecare product, perfumery raw material, flavored article, or food raw material to the phase consisting of the α-oxocarboxylic acid may result in chemical changes/damage to acid-sensitive compounds in the formulated perfume, body care product, cosmetic product, homecare product, perfumery raw material, flavored article, or food raw material, and consequently alter the organoleptic properties of the formulated perfume, body care product, cosmetic product, homecare product, perfumery raw material, flavored article, or food raw material.

Consequently, in some aspects presented herein, the α-oxocarboxylic acid is added at a rate that minimizes, or prevents the formation of the second phase consisting of the α-oxocarboxylic acid. Such rate of addition may be equal to the rate of the chemical reaction that reduces the POV of the formulated perfume, body care product, cosmetic product, homecare product, perfumery raw material, flavored article, or food raw material. Without intending to be limited to any particular theory, addition of the α-oxocarboxylic acid at the same rate as the chemical reaction may prevent the α-oxocarboxylic acid from accumulating and thereby keep the second phase volume minimized, which will reduce partitioning of the formulated perfume, body care product, cosmetic product, homecare product, perfumery raw material, flavored article, or food raw material into the highly acidic phase consisting of the α-oxocarboxylic acid.

Alternatively, effective dispersion of the α-oxocarboxylic acid in to the formulated perfume, body care product, cosmetic product, homecare product, perfumery raw material, flavored article, or food raw material may increase the rate of the chemical reaction that reduces the POV of the formulated perfume, body care product, cosmetic product, homecare product, perfumery raw material, flavored article, or food raw material, by increasing the surface area of contact between the two phases of the two phase system.

Examples of aspects where the solubility of the α-oxocarboxylic acid in the formulated perfume, body care product, cosmetic product, homecare product, perfumery raw material, flavored article, or food raw material is not low include, but are not limited to 2-oxo-valeric acid. Without intending to be limited to any particular theory, in aspects where the solubility of the α-oxocarboxylic acid in the formulated perfume, body care product, cosmetic product, homecare product, perfumery raw material, flavored article, or food raw material is not low may result in the formation of a single phase. Here, the added α-oxocarboxylic acid is soluble in the formulated perfume, body care product, cosmetic product, homecare product, perfumery raw material, flavored article, or food raw material being treated, and therefore will be diluted immediately upon addition. In this case, if the rate of addition is close to the rate of reaction, the α-oxocarboxylic acid will also be consumed as it is being added. The concentration of the α-oxocarboxylic acid will remain low, and acid-induced changes will be minimized.

In an alternate aspect, the concentration of un-reacted α-oxocarboxylic acid is minimized by using a buffer, wherein the α-oxocarboxylic acid is present as a deprotonated anion.

The anionic form of an α-oxocarboxylic acid will likely be unreactive toward a hydroperoxide relative to the protonated, acidic form. However, as the acidic form is consumed by reaction with hydroperoxides, the equilibrium of the α-oxocarboxylic acid-base pair will quickly reestablish itself in accordance with the pKa of α-oxocarboxylic acid; the anionic form will instantly capture a proton from the media to produce more of the hydroperoxide-reactive acidic form of the α-oxocarboxylic acid. In this way, the bulk acidity of the media can be maintained at a mild pH level, one that will not cause acid damage to the components of the formulated perfume, body care product, cosmetic product, homecare product, perfumery raw material, flavored article, or food raw material. But simultaneously, there will be a relatively low but fixed level of the α-oxocarboxylic acid in the reactive protonated form, replenished as soon as it is consumed from a sink of the relatively inert anionic form.

For example, using pyruvic acid for illustrative purposes only, pyruvic acid has a pKa of 2.50, buffering the formulated perfume, body care product, cosmetic product, homecare product, perfumery raw material, flavored article, or food raw material to pH 5.5 (a difference of 3 log units), would result in $10^3$ (or 1000) times the concentration of pyruvate anion, compared to pyruvic acid (as per the Henderson-Hasselbalch equation).

In one aspect, the concentration of the α-oxocarboxylic acid ranges from 0.001 to 10 weight percent, after addition to the formulated perfume, body care product, cosmetic product, homecare product, perfumery raw material, flavored article, or food raw material. In one aspect the concentration of the α-oxocarboxylic acid is 10 weight percent, after addition to the formulated perfume, body care product, cosmetic product, homecare product, perfumery raw material, flavored article, or food raw material. Alternatively, the concentration of the α-oxocarboxylic acid is 9, or 8, or 7, or 6, or 5, or 4, or 3, or 2, or 1, or 0.9, or 0.8, or 0.7, or 0.6, or 0.5, or 0.4, or 0.3, or 0.2, or 0.1, or 0.09, or 0.08, or 0.07, or 0.06, or 0.05, or 0.04, or 0.03, or 0.02, or 0.01, or 0.009, or 0.008, or 0.007, or 0.006, or 0.005, or 0.004, or 0.003, or 0.002, or 0.001 weight percent, after addition to the formulated perfume, body care product, cosmetic product, homecare product, perfumery raw material, flavored article, or food raw material.

The α-oxocarboxylic acid can be added directly to the formulated perfume, body care product, cosmetic product, homecare product, perfumery raw material, flavored article, or food raw material, or, alternatively, the α-oxocarboxylic acid can be diluted prior to addition to the formulated perfume, body care product, cosmetic product, homecare product, perfumery raw material, flavored article, or food raw material. Any diluent that may be used in perfumery may be used. Suitable diluents include, but are not limited to isopropanol, ethanol, diglyme, triethyleneglycol, and the like. The α-oxocarboxylic acid may be diluted 1:1, or 1:2, or 1:3, or 1:4, or more with the diluent.

Without intending to be limited by any particular theory, the choice of diluent may also influence the amount of the α-oxocarboxylic acid that may be added to the formulated perfume, body care product, cosmetic product, homecare product, perfumery raw material, flavored article, or food raw material. In addition, the choice of diluent may also influence the rate at which the α-oxocarboxylic acid that is be added to the formulated perfume, body care product, cosmetic product, homecare product, perfumery raw material, flavored article, or food raw material. For example, by way of illustration, using pyruvic acid as the α-oxocarboxylic acid, and ethanol as the solvent, the pyruvic acid must be added in an amount, and/or a at a rate that minimizes the formation of an ester with the ethanol.

The α-oxocarboxylic acid can be added to any volume of the formulated perfume, body care product, cosmetic product, homecare product, perfumery raw material, flavored article, or food raw material. For example, the α-oxocarboxylic acid can be added can be added to 1000 ml of formulated perfume, body care product, or perfumery raw material, or 900, or 800, or 700, or 600, or 500, or 400, or 300, or 200, or 100, or 90, or 80, or 70, or 60, or 50, or 40, or 30, or 20, or 10, or 9, or 8, or 7, or 6, or 5, or 4, or 3, or 2, or 1 ml of formulated perfume, body care product, cosmetic product, homecare product, perfumery raw material, flavored article, or food raw material.

In one aspect, the α-oxocarboxylic acid may be added to the formulated perfume, body care product, cosmetic product, homecare product, perfumery raw material, flavored article, or food raw material over 80 minutes. Alternatively, the α-oxocarboxylic acid may be added to the formulated perfume, body care product, cosmetic product, homecare product, perfumery raw material, flavored article, or food raw material over 70, or 60, or 50, or 40, or 30, or 20, or 10, or 9, or 8, or 7, or 6, or 5, or 4, or 3, or 2, or 1 minute(s).

In one aspect, the α-oxocarboxylic acid is added to the formulated perfume, body care product, cosmetic product, homecare product, perfumery raw material, flavored article, or food raw material at a rate of 0.25 ml per minute. In some aspects, the rate of addition is greater than 0.25 ml per minute. In some aspects, the rate of addition is less than 0.25 ml per minute.

Figure 2:
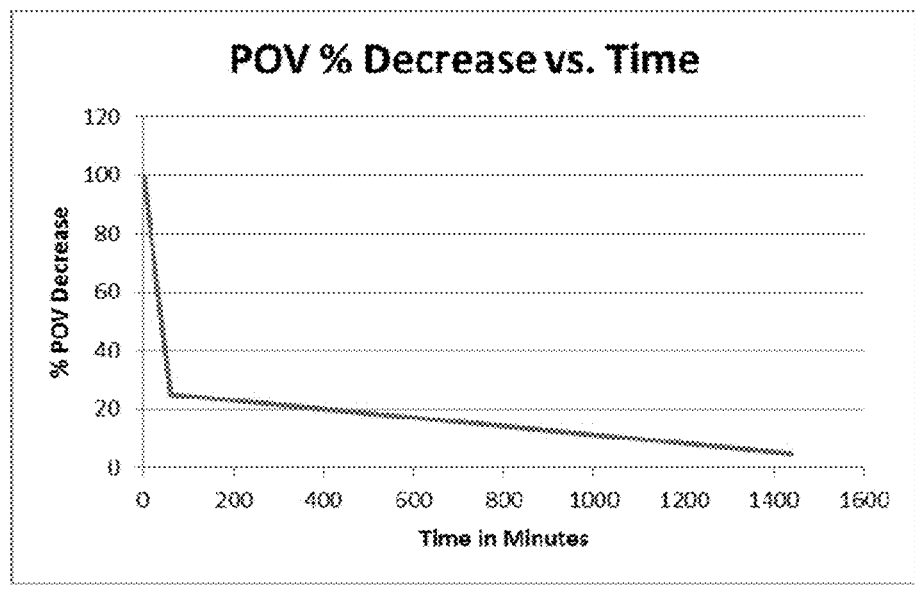
FIG. 2 shows a representation of the rate of reduction of POV in a perfumery raw material according to certain aspects presented herein.
Figure 3:
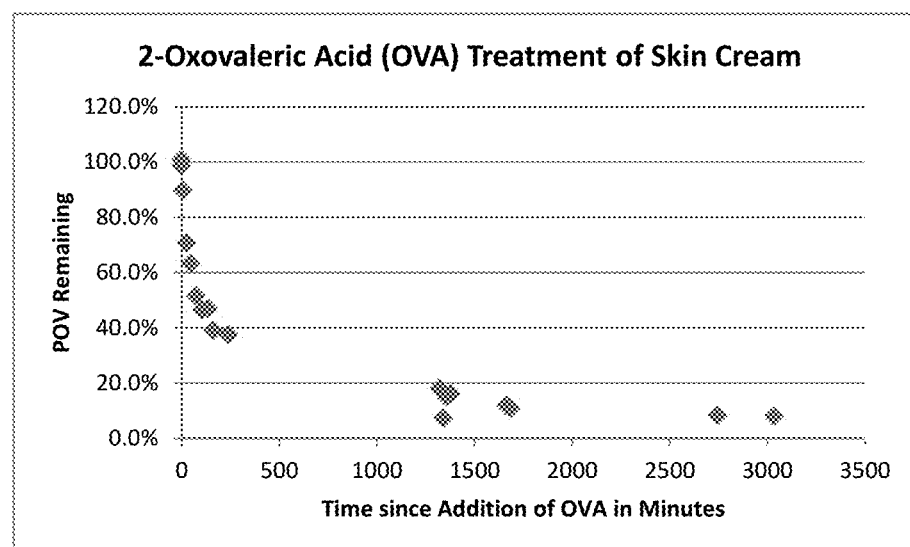
FIG. 3 shows POV of a skin cream by a method according to certain aspects presented herein.
Figure 4:
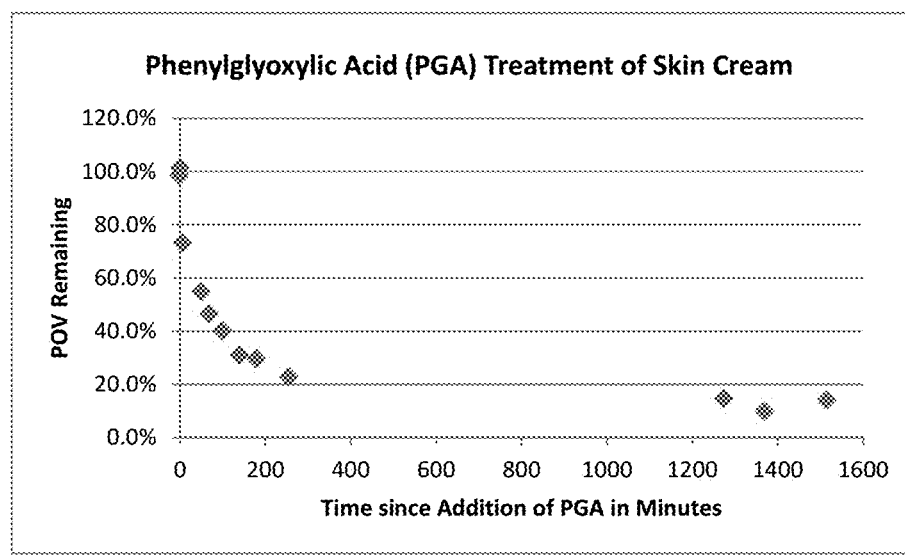
FIG. 4 shows POV of a skin cream by a method according to certain aspects presented herein.

In some aspects, the rate at which the α-oxocarboxylic acid is added to the formulated perfume, body care product, cosmetic product, homecare product, perfumery raw material, flavored article, or food raw material is constant. In some aspects, the rate at which the α-oxocarboxylic acid is added to the formulated perfume, body care product, cosmetic product, homecare product, perfumery raw material, flavored article, or food raw material varies. In one aspect, the α-oxocarboxylic acid is added to the formulated perfume, body care product, cosmetic product, homecare product, perfumery raw material, flavored article, or food raw material at a rate equal to the rate at which the α-oxocarboxylic acid is oxidized. In some aspects, the rate at which the α-oxocarboxylic acid is oxidized may be determined by measuring the POV in the treated formulated perfume, body care product, or perfumery raw material. Referring to FIGS. 2 to 4, by way of illustration, the rate of reduction of POV may have a first rate, which is greater than a second rate. In the aspect illustrated, the duration of the first rate is less than the duration of the second rate.

In an alternate aspect, the α-oxocarboxylic acid may be added, and subsequently quenched after a period of time. The α-oxocarboxylic acid may be quenched 80 minutes after addition to the substance. Alternatively, the α-oxocarboxylic acid may be quenched 70, or 60, or 50, or 40, or 30, or 20, or 10, or 9, or 8, or 7, or 6, or 5, or 4, or 3, or 2, or 1 minute(s) after addition to the substance.

In one aspect, the method further comprises removing the excess α-oxocarboxylic acid from the formulated perfume, body care product, cosmetic product, homecare product, perfumery raw material, flavored article, or food raw material having a POV of a pre-determined second lower level.

In one aspect, the excess α-oxocarboxylic acid is removed from the formulated perfume, body care product, cosmetic product, homecare product, perfumery raw material, flavored article, or food raw material via a liquid-liquid extraction.

In one aspect, the excess α-oxocarboxylic acid is removed from the formulated perfume, body care product, cosmetic product, homecare product, perfumery raw material, flavored article, or food raw material via a liquid-liquid extraction using water.

In one aspect, other byproducts of the reaction that reduces the POV of the formulated perfume, body care product, cosmetic product, homecare product, perfumery raw material, flavored article, or food raw material to the pre-determined second lower level are also removed by the liquid-liquid extraction. All byproducts, or, alternatively, a portion of the byproducts may be removed.

In one aspect, the method further comprises treating the formulated perfume, body care product, cosmetic product, homecare product, perfumery raw material, flavored article, or food raw material after removing the excess α-oxocarboxylic acid to reduce the acidity of the substance. In some aspects, the treatment comprises the addition of a buffer, such as, for example, triethanolamine, or N-methyldiethanolamine, and the like.

In one aspect, the substance is treated with a carbonate salt to reduce the acidity of the formulated perfume, body care product, cosmetic product, homecare product, perfumery raw material, flavored article, or food raw material.

In one aspect, the method for reducing the POV of a formulated perfume, body care product, cosmetic product, homecare product, perfumery raw material, flavored article, or food raw material comprises the steps of:
  a) introducing the formulated perfume, body care product, cosmetic product, homecare product, perfumery raw material, flavored article, or food raw material into a reaction vessel, wherein the formulated perfume, body care product, cosmetic product, homecare product, perfumery raw material, flavored article, or food raw material is under an inert gas, such as, for example, argon;
  b) introducing the α-oxocarboxylic acid to the formulated perfume, body care product, cosmetic product, homecare product, perfumery raw material, flavored article, or food raw material at a rate of 0.25 ml per minute, wherein the α-oxocarboxylic acid is diluted 1:4 with a diluent, wherein the α-oxocarboxylic acid to the formulated perfume, body care product, cosmetic product, homecare product, perfumery raw material, flavored article, or food raw material is constantly stirred during the introduction;
  c) introducing water and anhydrous sodium carbonate to the mixture and allowing the reaction to continue until there is no longer any visible evolution of $CO_2$; and
  d) discarding the aqueous layer, thereby obtaining a formulated perfume, body care product, cosmetic product, homecare product, perfumery raw material, flavored article, or food raw material with a POV having a pre-determined second lower level.

Examples of a method according to the aspect described above can be found in Examples 1 to 4 below.

In some aspects, the second phase of the α-oxocarboxylic acid in the formulated perfume, body care product, cosmetic product, homecare product, perfumery raw material, flavored article, or food raw material is a "leave-in" composition of the α-oxocarboxylic acid. Without intending to be limited to any particular theory, the amount α-oxocarboxylic acid present in the two phases is in equilibrium, and the reduction of POV may result in the α-oxocarboxylic acid moving from the phase consisting of α-oxocarboxylic acid, into the phase containing the formulated perfume, body care product, cosmetic product, homecare product, perfumery raw material, flavored article, or food raw material. One example of this aspect is described in Example 5 below.

In some aspects, the "leave-in" composition of the α-oxocarboxylic acid comprises a single phase composition with the formulated perfume, body care product, cosmetic product, homecare product, perfumery raw material, flavored article, or food raw material. In these aspects, the composition further comprises a buffer, wherein the pH is configured to maintain the majority of the α-oxocarboxylic acid present in a non-protonated form, wherein the non-protonated form is incapable of reacting with the chemical species that contribute to the POV of the composition (including peroxides, organic hydroperoxides, peroxyhemiacetals). Without intending to be limited to any particular theory, the amount of the α-oxocarboxylic acid present in non-protonated form is in equilibrium with an amount of amount of the α-oxocarboxylic acid present in protonated form, and the reduction of POV may result in the α-oxocarboxylic acid moving from the non-protonated from to the protonated form. One example of this aspect is described in Example 4 below.

In these instances, the "leave-in" compositions of the α-oxocarboxylic acid is capable of reducing POV for a prolonged period of time.

Accordingly, one aspect presented herein, provides a composition comprising: (a) a formulated perfume, body care product, cosmetic product, homecare product, perfumery raw material, flavored article, or food raw material, and (b) an α-oxocarboxylic acid, wherein the α-oxocarboxylic acid is present in the composition in an amount sufficient to decrease the POV from a first level to a pre-determined second lower level.

In one aspect, the α-oxocarboxylic acid is present in the composition in an amount sufficient to prevent the pre-determined second lower level from changing with time. The time may be hours, days, weeks, or longer.

One aspect presented herein, provides a composition comprising: (a) a formulated perfume, body care product, cosmetic product, homecare product, perfumery raw material, flavored article, or food raw material, and (b) an α-oxocarboxylic acid, wherein the α-oxocarboxylic acid is present in the composition in an amount sufficient to reduce, prevent, or ameliorate an increase in the POV of the formulated perfume, body care product, cosmetic product, homecare product, perfumery raw material, flavored article, or food raw material.

In one aspect, the concentration of the α-oxocarboxylic acid in the composition ranges from 0.001 to 10 weight percent.

In one aspect, the α-oxocarboxylic acid is selected from the group consisting of: pyruvic acid, 2-oxovaleric acid, phenylglyoxylic acid, 2-oxobutyric acid, 2-oxo-2-furanacetic acid, oxaloacetic acid, α-ketoglutaric acid, 2-oxopentandioate, indole-3-pyruvic acid, 2-thiopheneglyoxylic acid, trimethylpyruvic acid, 2-oxoadipic acid, 4-hydroxyphenylpyruvic acid, phenylpyruvic acid, 2-oxooctanoic acid, and mixtures thereof.

In one aspect, the perfumery raw material is citrus oil.

An example of a composition according to the aspect described above can be found in Example 5 below.

In some aspects, the at least one α-oxocarboxylic acid, or a salt thereof may be applied to, or incorporated into, or covalently bound to a solid substrate, wherein the solid substrate comprising the at least one α-oxocarboxylic acid, or a salt thereof is used to treat a formulated perfume, body care product, cosmetic product, perfumery raw material, flavored article, or food raw material.

Any inert, finely divided or high surface area material may be used as the solid support. Examples include, but are not limited to: metals, glass, expanded ceramics, plastics, or inorganic solids. In addition, the solid support may comprise the bottom and/or the walls of a vessel containing the formulated perfume, body care product, cosmetic product, perfumery raw material, flavored article, or food raw material.

In some aspects, the solid support has a high surface are:volume ratio. Examples of such solid supports include, but are not limited to steel wool. An example of a composition treated according to the aspect employing a solid support as described above can be found in Example 24 below.

The present invention is best illustrated but is not limited to the following examples.

EXAMPLES

Example 1

Reduction of POV in Citrus Oil According to One Aspect Presented Herein Using Pyruvic Acid 50 mL of mixed citrus oils (orange, lemon, lime, mandarin, bergamot, and tangerine) were placed in a 100 round bottom flask at room temperature, along with a stir bar and an argon gas blanket.

A 4:1 v/v isopropanol/pyruvic acid solution was made. 20 mL of this pyruvic acid solution was dripped into the stirred citrus oils at a rate of 0.25 mL/minute via the use of a syringe pump.

When the addition was complete, 10 mL of water and 100 mg of anhydrous sodium carbonate was added to the flask, and the stirring was maintained. When the visible evolution of $CO_2$ had stopped (about 2-4 minutes), the aqueous layer was removed with a pipette and discarded. POV measurements were made on the mixed citrus oil before and after the pyruvic acid treatment.

POV before treatment was 27.261 mEq/L, and the POV after treatment was 4.786 mEq./L. This was about an 82% reduction in POV.

Example 2

Reduction of POV in Limonene According to One Aspect Presented Herein Using 2-Oxo-Valeric Acid 10 mL of autoxidized limonene was placed in a 30 mL glass vial at room temperature, along with a stir bar and an argon gas blanket. 100 µL of 2-oxovaleric acid was added. The vial was shaken once and allowed to stand for 50 minutes. No further treatment was done prior to the POV testing. POV measurements were made on the limonene before and after the 2-oxovaleric acid treatment. POV before treatment was 65.97 mEq./L, and POV after treatment was 17.21 mEq./L. This was an approximately 74% reduction in POV.

Example 3

Reduction of POV in Limonene According to One Aspect Presented Herein Using 2-Oxo-Butyric Acid 20 mL of autoxidized limonene was placed in a 30 mL glass vial at room temperature, along with a stir bar and an argon gas blanket. 250 µL of 2-oxobutyric acid was added. The vial was shaken once and allowed to stand, while being monitored for POV value as a function of time. The data collected is shown in the table below.

| Time (in min.) since addition of 2-oxobutryric acid | POV (in mEq/L) | POV reduction (in %) |
|---|---|---|
| Untreated | 66.245 | 0.0 |
| 3 | 43.680 | 34.1 |
| 20 | 22.140 | 66.6 |
| 35 | 22.681 | 65.8 |
| 44 | 19.968 | 69.9 |
| 66 | 21.406 | 67.7 |
| 116 | 19.576 | 70.4 |
| 176 | 20.964 | 68.4 |

The results showed an initial rapid reduction in POV, followed by decline in the rate of POV reduction. This may be due to reagent depletion, but the loss of POV is not sufficient to fully account on a molar basis for all of the added 2-oxobutyric acid. It may be that some hydroperoxides are destroyed very quickly, and other oxidants are destroyed much more slowly. When an additional 500 µL of 2-oxobutyric acid was added, and the sample allowed to stand for an additional 24 hours, the measured POV was 8.577 mEq./L (87.1% total reduction).

Example 4

Reduction of POV in Limonene According to One Aspect Presented Herein Using 2-Phenylglyoxylic Acid 20 mL of autoxidized limonene was placed in a 30 mL glass vial at room temperature, along with a stir bar and an argon gas blanket. 200 mg of phenylglyoxylic acid was added, which dissolved. The vial was shaken once and allowed to stand, while being monitored for POV value as a function of time. The data collected is shown in the table below.

| Time (in min.) since addition of phenylglyoxylic acid | POV (in mEq/L) | POV reduction (in %) |
|---|---|---|
| Untreated | 44.795 | 0.0 |
| 40 | 37.035 | 17.3 |
| 150 | 34.086 | 23.9 |
| 190 | 29.963 | 33.1 |
| 2880 (48 hrs) | 17.265 | 61.5 |

Example 5

Reduction of POV in Limonene According to One Aspect Presented Herein Using 2-Oxo-2-Furanacetic Acid 20 mL of mixed citrus oil was placed in a 30 mL glass vial at room temperature, along with a stir bar and an argon gas blanket. 400 mg of α-oxo-2-furanacetic acid was added. The vial was shaken once and allowed to stand, while being monitored for POV value as a function of time. The majority of the added α-oxo-2-furanacetic acid did not dissolve, so the limited solubility of the acid will likely act as a controlled release mechanism; as the α-oxo-2-furanacetic acid in solution is consumed by hydroperoxides, more will likely dissolve in accordance will the solubility constant. In this way, the undissolved solid acts as a sink to maintain a steady, low concentration of α-oxo-2-furanacetic acid dissolved in the mixed citrus oil.

In this case, because the time between measurements was relatively long (days instead of minutes), there is the possibility that the untreated mixed citrus oil will oxidize further during the course of the experiment. Therefore, the POV of the treated oil was still compared with the POV of the untreated oil, but the measurement of the untreated oil was re-determined at each time point (rather than just a single, initial value being used). The data collected is shown in the table below.

| Time (in days) since addition of α-Oxo-2-furanacetic acid | Untreated POV (in mEq/L) | Treated POV (in mEq/L) | POV reduction (in %) |
|---|---|---|---|
| Untreated | 20.593 | 20.593 | 0.0 |
| 2 | 25.366 | 18.566 | 26.8 |
| 4 | 28.581 | 17.193 | 39.8 |
| 44 | 29.119 | 1.106 | 96.2 |

Example 6

Reduction of POV in a Skin Cream Formulation According to One Aspect Presented Herein Using 2-Oxovaleric Acid or Phenylglyoxylic Acid A skin cream formulation comprising of 0.5 parts cetylstearyl alcohol, 6.0 parts wool wax alcohol, and 93.5 parts white petroleum jelly was created as per the German Pharmacopoeia DAB 2008.

The skin cream was divided into two separate preparations. A highly oxidized limonene sample was added to both preparations, with the first preparation receiving a concentration of oxidized limonene approximately one third of the concentration of the oxidized limonene in the second preparation. Analysis of the oxidized limonene sample showed the sample to contain a mixture of limonene hydroperoxide isomers.

The initial POV of both the first and second skin cream preparations was taken, prior to treatment with 2-oxovaleric acid or phenylglyoxylic acid as follows: 2-oxovaleric acid (second preparation), or phenylglyoxylic acid (first preparation) was thoroughly blended into the skin cream preparations. The POV of the preparations were measured, during addition of the 2-oxovaleric acid. After addition of the 2-oxovaleric acid or phenylglyoxylic acid, the treated preparations were allowed to stand at room temperature. The POV data obtained was corrected for the exact weight of the aliquot of cream titrated at each individual time point, and normalized as a percentage to the starting POV.

The second preparation, containing the highest amount of the oxidized limonene sample was treated with approximately 2.3% w/w 2-oxovaleric acid. The results are shown below in FIG. 3.

The first preparation, containing the lowest amount of the oxidized limonene sample was treated with approximately 3.9% w/w 2-phenylglyoxylic acid. The results are shown below in FIG. 4.

Example 7

Formation of a Diammonium Salt Via the Reaction of α-Ketoglutaric Acid (CAS #328-50-7) and N-Methyl Diethanolamine (NMDEA, CAS #105-59-9) in a 1:2 Molar Ratio 1.461 g (0.01 moles) of α-ketoglutaric acid was dissolved in 10 mL of dry acetone to give a clear solution. This solution was added as one portion to 2.384 g (0.02 moles) of neat NMDEA. The opaque, white emulsion was vortexed vigorously for 3-4 minutes, during which time a second phase had coalesced. The mixture was placed in a freezer for at least 30 minutes, causing the bottom phase to thicken to a waxy solid. While still cold, the top layer was easily removed via decantation or pipet, and discarded. Residual acetone was removed from the bottom, product layer via a stream of nitrogen followed by treatment in a vacuum oven at room temperature. This resulted in a clear, faint yellow, highly viscous oil at room temperature containing the diammonium salt (AKG-DiNMDEA salt).

A model perfume was made using 90/10 v/v ethanol/water as a solvent, and a mixture of orange, grapefruit, and bergamot oils as the perfume oil. The mixed citrus oil was loaded into the solvent at approximately 19.4% v/v (6 mL oil into 25 mL solvent). Approximately 400 mg (2.0% w/v) of the AKG-DiNMDEA salt was dissolved in 20 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Minutes | POV of Treated Perfume | POV of Untreated Perfume |
|---|---|---|
| 0.0 | 12.39 mmol/L | 12.39 mmol/L |
| 70 | 8.07 | — |
| 90 | 6.16 | — |
| 1150 | 1.38 | — |
| 1165 | 1.06 | — |
| 1180 | 0.85 | — |
| 1195, 1210 | — | 12.31, 13.60 |
| 1220 | 0.78 | — |
| 1400 | — | 13.38 |
| 1420 | 0.77 | — |
| 1440 (24 hours) | 0.79 | — |

These data show a reduction in the POV of approximately 94%, 24 hours after addition of the AKG-DiNMDEA salt.

In addition to the treatment done in a model perfume as described above, a similar experiment was done in mixed citrus oil. A sample of mixed citrus oil was made by combining lime, orange, grapefruit, lemon, mandarin, tangerine, and bergamot oils, so that a variety of terpene hydroperoxides would be present in the treated mixture being tested. Approximately 200 mg (1.0% w/v) of the AKG-DiNMDEA salt was added to 20 mL of the mixed citrus oil. The salt did not appear to dissolve completely even after vigorous mixing. Nonetheless, POV measurements were taken as a function of time after the addition. An untreated mixed citrus oil sample was handled similarly to the treated oil and also tested, because the POV can rise rapidly with handling of the sample (opening the bottle, agitation, etc.). The results are shown in the table below.

| Time in Minutes | POV of Treated Perfume | POV of Untreated Perfume |
|---|---|---|
| 0.0 | 10.37 mmol/L | 10.37 mmol/L |
| 90 | 5.42 | — |
| 110 | 5.36 | — |
| 135 | — | 11.28 |
| 150 (2.5 hrs) | 4.87 | — |
| 1240 | 3.91 | — |
| 1250 | 4.40 | — |

| Time in Minutes | POV of Treated Perfume | POV of Untreated Perfume |
| --- | --- | --- |
| 1280 | 3.96 | — |
| 1505 (25 h & 5 min) | 4.52 | — |
| 1545 | 4.25 | — |

This represents only a moderate-to-good improvement in the POV status of the oil; a 59% reduction in POV after over a day of treatment time. This is likely due to the poor solubility of the 2-oxoacid salt in the citrus oil.

Example 8

Formation of a Diammonium Salt Via the Reaction of α-Ketoglutaric Acid (CAS #328-50-7) and N,N-Dimethyldodeclyamine (DiMeC12A, CAS #112-18-5) in a 1:2 Molar Ratio 1.461 g (0.01 moles) of α-ketoglutaric acid was dissolved in 6 mL of dry acetone. This solution was added dropwise with stirring over the course of 1-2 minutes to a separate solution of 4.268 g (0.02 moles) of N, N dimethyldodecylamine in 6 mL of dry acetone. No visible indication of reaction was seen except that the combined solution warmed up to about 35-40° C. The mixture was shaken briefly but vigorously, and cooled in a freezer for 30 minutes. Even when cold, still no precipitation of product occurred, but when the mixture was shaken again, the entire mass almost instantly solidified into a solid, white, waxy substance. This solid was warmed up to 30-35° C. to re-liquefy the product so that entrapped acetone could be removed via a stream of nitrogen followed by treatment in a vacuum oven at room temperature. This gave a white, waxy solid containing the diammonium salt (AKG-DiMeC12A salt).

A model perfume was made using 90/10 v/v ethanol/water as a solvent, and a mixture of orange, grapefruit, and bergamot oils as the perfume oil. The mixed citrus oil was loaded into the solvent at approximately 19.4% v/v (6 mL oil into 25 mL solvent). Approximately 400 mg (2.0% w/v) of the AKG-DiMeC12A salt was dissolved in 20 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Minutes | POV of Treated Perfume | POV of Untreated Perfume |
| --- | --- | --- |
| 0.0 | 12.74 mmol/L | 12.74 mmol/L |
| 35 | 8.31 | — |
| 45 | 8.35 | — |
| 70 | 6.77 | — |
| 130 | 6.54 | — |
| 145 | 5.82 | — |
| 180 | 4.89 | — |
| 210 | 4.51 | — |
| 240 (4 hours) | 4.15 | — |
| 270 | 3.49 | — |
| 4320 (3 days, 72 hours) | 0.0 indistinguishable from blank | 14.43 |

In addition to the treatment done in a model perfume as described above, a similar experiment was done in mixed citrus oil. A sample of mixed citrus oil was made by combining lime, orange, grapefruit, lemon, mandarin, tangerine, and bergamot oils, so that a variety of terpene hydroperoxides would be present in the treated mixture being tested. Approximately 200 mg (1.0% w/v) of the AKG-DiMeC12A salt was dissolved in 20 mL of the mixed citrus oil, and POV measurements were taken as a function of time after the addition. An untreated mixed citrus oil sample was handled similarly to the treated oil and also tested, because the POV can rise rapidly with handling of the sample (opening the bottle, agitation, etc.). The results are shown in the table below.

| Time in Minutes | POV of Treated Perfume | POV of Untreated Perfume |
| --- | --- | --- |
| 0.0 | 9.53 mmol/L | 9.53 mmol/L |
| 90 | 3.32 | — |
| 95 | 2.32 | — |
| 105 | 2.63 | — |
| 130 | 2.68 | — |
| 150 (2.5 hours) | 2.28 | — |
| 250 | 1.81 | — |
| 260 | 1.41 | — |
| 4320 (3 days, 72 hours) | 1.50 | 13.58 |

These data represent an 89.0% reduction in the POV, within 72 hours (3 days) after the addition of AKG-DiMeC12A. It appears that the AKG-DiMeC12A may have been depleted after the 260 minute time point, because no further reaction happened even after an extended period.

Surface Tension Measurements of Aqueous AKG-DiMeC12A: In order to evaluate the surfactant properties of AKG-DiMeC12A, the reduction in surface tension that it causes in aqueous solution versus pure water was measured. The measurement was made on a Kruss DSA100S Tensiometer by the pendant drop method. A 0.14 weight % solution of AKG-DiMeC12A in water was used for the measurement. This concentration was chosen so the results could be compared to the literature value for known surfactant sodium dodecyl sulfate (SDS) at 5 mM, which is approximately 0.15 weight %. The results show that AKG-DiMeC12A has significant surfactant properties:

Pure water—71.57 mN/m

AKG-DiMeC12A—32.08 mN/m

For comparison, SDS at 5 mM concentration (approximately 0.15 weight %, which is very close to the 0.14 weight % used here) at 273K, has an air-water surface tension in the range of 33.5 to 35.5 mN/m depending on the pH (see Hemainz, F. et al, Colloids Surf. A, 2002, 196, 19-24).

Example 9

Formation of a Diammonium Salt Via the Reaction of α-Ketoglutaric Acid and (CAS #328-50-7) and 2-(dimethylamino(ethanol (Deanol, CAS #108-01-0) in a 1:2 Molar Ratio 1.461 g (0.01 moles) of α-ketoglutaric acid was dissolved in 10 mL of dry acetone to give a clear solution. This solution was added over the course of 1-2 minutes with stirring to 1.783 g (0.02 moles) of neat 2 dimethylaminoethanol ("Deanol"). The opaque, white emulsion was vortexed vigorously for a minute, during which time a second phase had coalesced. The mixture was placed in a freezer overnight, causing the bottom phase to thicken to extremely viscous, hazy oil. While still cold, the top layer was easily removed via decantation or pipet, and discarded. Residual acetone was removed from the bottom product layer via a stream of nitrogen followed by treatment in a vacuum oven at room temperature. This produced clear, colorless, viscous oil at room temperature containing the diammonium salt (AKG DiDeanol salt).

A model perfume was made using 90/10 v/v ethanol/water as a solvent, and a mixture of orange, grapefruit, and bergamot oils as the perfume oil. The mixed citrus oil was loaded into the solvent at approximately 19.4% v/v (6 mL oil into 25 mL solvent). Approximately 200 mg (1.0% w/v) of the AKG DiDeanol salt was dissolved in 20 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Minutes | POV Treated Perfume | POV Untreated Perfume |
| --- | --- | --- |
| 45 | — | 11.73 mmol/L |
| 60 | 5.95 mmol/L | — |
| 75 | 5.66 | — |
| 115 | 4.96 | — |
| 195 | 3.20 | — |
| 210 | 3.08 | — |
| 270 | — | 12.25 |
| 300 (5 hours) | 2.31 | — |
| 370 | 1.73 | — |
| 380 | 1.72 | — |
| 390 | — | 11.70 |
| 1440 (24 hours) | 0.0 indistinguishable from blank | 11.79 |

Example 10

Formation of an Ammonium Salt Via the Reaction of Pyruvic Acid (CAS #328-50-7) and N-Methyl Diethanolamine (NMDEA, CAS #105-59-9) in a 1:1 Molar Ratio 2.642 g (0.03 moles) of pyruvic acid was dissolved in 5 mL of dry acetone to give a clear solution. This solution was added dropwise with stirring over the course of 1-2 minutes to a second solution made from 3.575 g (0.03 moles) of NMDEA and 5 mL of dry acetone. The resulting mixture became warm (approximately 35-45° C.) and hazy as the acid solution was added. The milky emulsion was vortexed vigorously for a minute, during which time a second phase had coalesced. The mixture was placed in a freezer for at least 1 hour, causing the bottom phase to increase significantly in viscosity, but not solidify. While still cold, the top layer was easily removed via decantation or pipet, and discarded. Residual acetone was removed from the bottom product layer via a stream of nitrogen followed by treatment in a vacuum oven at room temperature. This gave clear, golden colored, highly viscous oil at room temperature containing the diammonium salt (PA-NMDEA salt).

A model perfume was made using 90/10 v/v ethanol/water as a solvent, and a mixture of lime, orange, grapefruit, and bergamot oils as the perfume oil. The mixed citrus oil was loaded into the solvent at approximately 16.7% v/v (40 mL oil into 200 mL solvent, 240 mL total perfume). Approximately 150 mg (1.0% w/v) of the PA-NMDEA salt was dissolved in 15 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Hours | POV Treated Perfume | POV Untreated Perfume |
| --- | --- | --- |
| 0.0 | — | 5.55 mmol/L |
| 1.8 | 3.48 mmol/L | — |
| 71.5 | 1.01 | — |
| 72.5 | — | 6.66 |
| 73.3 | 0.58 | — |
| 74.7 | — | 6.58 |

These data suggest that the PA-NMDEA was depleted at the 73.3 hour mark, because the POV of the sample never went any lower after that, even at extended reaction times. This represents >90% reduction in POV; the average untreated oil after 3 days was (6.66+6.58)/2=6.62 mmol/L, so 0.58/6.62×100=8.76% remaining, or 91.2% reduction in POV).

Example 11

Formation of an Ammonium Salt Via the Reaction of Phenylglyoxylic Acid (PhGA, CAS #611-73-4) and N-Methyl Diethanolamine (NMDEA, CAS #105-59-9) in a 1:1 Molar Ratio 1.501 g (0.01 moles) of PhGA was dissolved in 5 mL of dry acetone to give a clear solution. This solution was added in one portion to a second solution made from 1.192 g (0.01 moles) of NMDEA and 5 mL of dry acetone. The resulting mixture became warm (approximately 30-35° C.) and turned pale yellow in color, but no haze or precipitate formed. The solution was vortexed vigorously for a minute, and placed in a freezer for 30 minutes. Still no precipitate or second layer formed, but the solution was apparently supersaturated. An attempt was made to remove the solvent acetone via a stream of nitrogen, but almost instantly as the nitrogen stream touched the solution, a thick paste of white crystalline material formed. The crystals began to re-dissolve back into the acetone as the mixture warmed to room temperature. The product was re-frozen, causing re-precipitation of the highly crystalline product, and the supernatant acetone was removed while still cold via pipet as much as possible. Residual acetone was then removed under a stream of nitrogen to give pure white, needle shaped crystals. The crystalline product containing the diammonium salt (PhGA-NMDEA salt) was extremely hygroscopic, and would liquefy very rapidly if exposed to ambient atmosphere; the white mass of needles had to be kept under vacuum or a rigorous nitrogen blanket to remain crystalline. A weight/yield was not obtained due to the hygroscopicity.

A model perfume was made using 90/10 v/v ethanol/water as a solvent, and a mixture of lime, orange, grapefruit, and bergamot oils as the perfume oil. The mixed citrus oil was loaded into the solvent at approximately 16.7% v/v (40 mL oil into 200 mL solvent, 240 mL total perfume). Approximately 150 mg (1.0% w/v) of the PhGA-NMDEA salt was dissolved in 15 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Hours | POV Treated Perfume | POV Untreated Perfume |
|---|---|---|
| 0.0 | — | 5.55 mmol/L |
| 1.8 | 4.87 mmol/L | — |
| 71.5 (~3 days) | 4.61 | — |
| 72.5 | — | 6.66 |
| 73.3 | 4.18 | — |
| 74.7 | — | 6.58 |
| 243 (~10 days) | 2.62 | 8.37 |

These data suggest that while the phenylglyoxylic acid moiety does work to lower the POV in the model perfume, it is less reactive than the non-aryl pyruvates studied. This difference in reactivity may be useful in some circumstances.

Example 12

Reduction of POV in Sunflower Oil According to One Aspect Presented Herein Using 2-Oxovaleric Acid 25 mL of sunflower oil (from an off-the-shelf, opened 1 quart container with approximately 25% atmospheric headspace; storage time unknown) was placed in a 30 mL vial at room temperature. 250 µL of 2-oxovaleric acid was added. The vial was shaken and allowed to stand at ambient temperature in laboratory lighting on the benchtop. No further treatment was done prior to the POV testing.

POV measurements were made on the sunflower oil before and after the 2-oxovaleric acid treatment. The untreated oil was also re-measured periodically for comparison, since opening of the bottle replenishes atmospheric headspace and can cause the POV of the bottle contents to rise. The % reduction was always calculated versus the most recent POV value on the untreated oil, and if multiple measurements were made, an averaged value (shown in parentheses) was used for the calculation. The results are shown in the table below.

| Time (in varying units) since addition of 2-oxovaleric acid | POV (in mmol/L) | POV reduction (in %) |
|---|---|---|
| Untreated (time 0) | 9.00, 8.68, 8.74 (8.81) | N/A |
| 30 minutes | 7.38 | 16.2 |
| 50 minutes | 7.84 | 11.0 |
| 23 hours | 4.95, 4.67 (4.81) | 45.4 |
| Untreated (46 hours) | 11.87, 10.35 (11.11) | N/A |
| 46 hours | 5.34, 5.10 (5.22) | 53.0 |
| Untreated (15 days) | 11.89, 12.16, 12.85 (12.30) | N/A |
| 15 days | 2.27, 2.05, 1.99 (2.10) | 82.9 |

N/A = Not applicable

The untreated sunflower oil increased in POV by nearly 40% (12.30/8.81 mmol/L×100=139.6%) from merely sitting at room temperature in the bottle for 15 days, with a headspace that had been replenished with ambient atmosphere during the brief opening required to do each sampling.

Conversely, the treatment of sunflower oil with 0.83% v/v of 2-oxovaleric acid resulted in a 82.9% reduction in POV after 15 days versus the untreated oil.

Example 13

Formation of an Ammonium Salt Via the Reaction of Phenylpyruvic Acid (CAS #156-06-9) and N,N-Dimethyldecylamine (DiMeC10A, CAS #1120-24-7) in a 1:1 Molar Ratio 3.707 g (0.02 moles) of phenylpyruvic acid was dissolved in 10 mL of dry acetone to give a clear solution. A separate solution was made from 3.283 g (0.02 moles) of N,N-dimethyldecylamine in 10 mL of dry acetone. The amine solution was added dropwise with stirring over the course of 2-3 minutes to the phenylpyruvic acid solution; no visible indication of reaction was seen, and no warming was noticeable. The mixture was shaken briefly but vigorously, and cooled in a freezer for 30 minutes. A thick network of white, flocculent, fine crystals was formed, and a small amount of acetone was decanted off of the solid mass while still cold and discarded. The majority of the solvent acetone appeared entrapped within the crystalline network and was removed via a stream of nitrogen followed by treatment in a vacuum oven at room temperature. This gave a slightly off-white, fluffy crystalline solid in quantitative yield.

Reduction of POV in Sunflower Oil According to One Aspect Presented Herein Using the Diammonium Salt Formed Via the Reaction of Phenylpyruvic Acid and N,N-Dimethyldecylamine (Referred to Herein as DiMeC10A-PhPA): 15 mL of sunflower oil that had been stored in a plastic bottle at room temperature for 1 year, but never opened during this storage period, was placed into a 30 mL glass vial, and 0.3032 g of DiMeC10A-PhPA was added to it. The majority of the salt dissolved, but some undissolved solid remained. The mixture was allowed to stand on the benchtop in ambient laboratory light at room temperature, and POV measurements were taken periodically. The results are shown in the table below.

| Time since addition of DiMeC10A-PhPA | POV (mmol/L) of untreated oil | POV (mmol/L) of treated oil | % Reduction in POV |
|---|---|---|---|
| 55 minutes | 16.55 | 3.78 | 77.2% |
| 140 minutes | — | 0.00(*) | 100% |
| 1320 mins (22 hrs) | 16.57 | 0.00(*) | 100% |
| 23 days | 18.65 | 0.00(*) | 100% |

(*)Indistinguishable from BLANK

This phenyl pyruvate salt produced extremely rapid reduction of the sunflower oil POV.

Reduction of POV in a Model Perfume According to One Aspect Presented Herein Using the Diammonium Salt Formed Via the Reaction of Phenylpyruvic Acid and N,N-Dimethyldecylamine (Referred to Herein as DiMeC10A-PhPA): A model perfume was made using 90/10 v/v ethanol/water as a solvent, and a mixture of lime, orange, grapefruit, and bergamot oils as the perfume oil. The mixed citrus oil was loaded into the solvent at approximately 16.7% v/v (40 mL oil into 200 mL solvent, 240 mL total perfume). Approximately 164 mg (1.1% w/v) of the PhPA-DiMeC10A salt was dissolved in 15 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Hours/ Days | POV of Treated Perfume | POV of Untreated Perfume |
| --- | --- | --- |
| 0.0 | 9.44 mmol/L | 9.44 mmol/L |
| 0.5 hours | 5.7 | — |
| 1 hour | — | 9.8 |
| 4 hours | 4.58 | 9.8 |
| 1 day | 3.1 | 9.66 |
| 2 days | 2.38 | 10.60 |
| 4 days | 1.98 | 10.12 |
| 7 days | 1.33 | 10.38 |

The results shown above represent a 87.2% reduction in POV relative to untreated material 7 days after addition of PhPA-DiMeC10A.

Example 14

Formation of an Ammonium Salt Via the Reaction of α-Oxo-2-Furanacetic Acid (CAS #1467-70-5) and N, N-Dimethyldecylamine (DiMeC10A, CAS #1120-24-7) in a 1:1 Molar Ratio 2.114 g (0.015 moles) of alpha-oxo-2-furanacetic acid was dissolved in 10 mL of dry acetone. The alpha-oxo-2-furanacetic acid was used as received from the supplier (a greyish-tan colored crystalline solid), and gave a dark brown solution containing a small quantity of undissolved flocculent material. It was decided to proceed with the "as is" material for preliminary screening, and a purified starting material could be made at a later time if the screening results so indicated.

A separate solution was made from 2.780 g (0.015 moles) of N,N-dimethyldecylamine in 10 mL of dry acetone. The amine solution was added dropwise with stirring over the course of 5 minutes to the crude alpha-oxo-2-furanacetic acid solution; no visible indication of reaction was seen, and no warming was noticeable. The mixture was shaken briefly but vigorously, and cooled in a freezer for 30 minutes. Even when cold, still no precipitation of product occurred, so the acetone was removed via a stream of nitrogen followed by treatment in a vacuum oven at room temperature. This gave brown, viscous oil in quantitative yield that crystallized to a tan solid after standing at freezer temperature for several days.

Reduction of POV in Sunflower Oil According to One Aspect Presented Herein Using the Diammonium Salt Formed Via the Reaction of alpha-oxo-2-furanacetic Acid and N, N-Dimethyldecylamine (Referred to Herein as FAA-DiMeC10A): 15 mL of sunflower oil that had been stored in a plastic bottle at room temperature for 1 year, but never opened during this storage period, was placed into a 30 mL glass vial, and 0.3358 g of FAA-DiMeC10A was added to it. The majority of the salt dissolved, but a small amount of dark brown insoluble droplets remained. The mixture was allowed to stand on the benchtop in ambient laboratory light at room temperature, and POV measurements were taken periodically. The results are shown in the table below.

| Time since addition of FAA-DiMeC10A | POV (mmol/L) of untreated oil | POV (mmol/L) of treated oil | % Reduction in POV |
| --- | --- | --- | --- |
| 85 minutes | 16.55 | 5.16 | 68.8% |
| 140 minutes | — | 2.97 | 82.1% |
| 1320 mins (22 hrs) | 16.57 | 0.43 | 97.4% |
| 23 days | 18.65 | 0.00(*) | 100% |

(*)Indistinguishable from BLANK

Reduction of POV in a Model Perfume According to One Aspect Presented Herein Using the Diammonium Salt Formed Via the Reaction of Alpha-Oxo-2-Furanacetic Acid and N, N-Dimethyldecylamine (Referred to Herein as FAA-DiMeC10A): A model perfume was made using 90/10 v/v ethanol/water as a solvent, and a mixture of lime, orange, grapefruit, and bergamot oils as the perfume oil. The mixed citrus oil was loaded into the solvent at approximately 16.7% v/v (40 mL oil into 200 mL solvent, 240 mL total perfume). Approximately 150 mg (1.0% w/v) of the FAA-DiMeC1OA salt was dissolved in 15 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Days | POV of Treated Perfume | POV of Untreated Perfume |
| --- | --- | --- |
| 0.0 | — | 5.15 mmol/L |
| 1 | 5.06 mmol/L | 6.31 |
| 2 | 4.89 | 6.77 |
| 4 | 4.68 | 7.14 |
| 7 | 4.28 | 7.13 |

The results shown above represent a 40.0% reduction in POV relative to untreated material 7 days after addition of FAA-DiMeC1OA. It appears that while the α-oxo-2-furanacetic acid moiety does work to lower the POV in the model perfume, it is less reactive/slower than the non-aryl α-oxo-carboxylic acids studied.

Example 15

Formation of a Diammonium Salt Via the Reaction of α-Ketoglutaric Acid (CAS #328-50-7) and tris[2-(2-(methoxyethoxy)ethyl]amine (CAS #70384-51-9) in a 1:2 Molar Ratio 2.922 g (0.02 moles) of alpha-ketoglutaric acid was dissolved in 10 mL of dry acetone. A separate solution was made from 12.937 g (0.04 moles) of tris[2-(2-(methoxyethoxy)ethyl]amine (TMEEA) in 5 mL of dry acetone. The amine solution was added dropwise with stirring over the course of 2 minutes to the AKG solution; no visible indication of reaction was seen, but the resulting mixture became slightly warm (approximately 35-45° C.). The mixture was shaken briefly but vigorously, and cooled in a freezer for 30 minutes. Even when cold, still no precipitation of product occurred, so the acetone was removed via a stream of nitrogen followed by treatment in a vacuum oven at room temperature. This gave a clear, golden-brown colored, slightly viscous oil in quantitative yield.

Reduction of POV in Sunflower Oil According to One Aspect Presented Herein Using the Diammonium Salt Formed Via the Reaction of Alpha-Ketoglutaric Acid and tris[2-(2-(methoxyethoxy)ethyl]amine (Referred to Herein as AKG-diTMEEA): 15 mL of sunflower oil that had been stored in a plastic bottle at room temperature for 1 year, but never opened during this storage period, was placed into a 30 mL glass vial, and 0.5081 g of AKG-diTMEEA was added to it. The higher than usual weight of this compound was used because of its' very high molecular weight (792.96 g/mole). This salt dissolved totally to give a clear, golden-brown oil. The solution was allowed to stand on the benchtop in ambient laboratory light at room temperature, and POV measurements were taken periodically. The results are shown in the table below.

| Time since addition of AKG-diTMEEA | POV (mmol/L) of untreated oil | POV (mmol/L) of treated oil | % Reduction in POV |
|---|---|---|---|
| 65 minutes | 16.55 | 11.72 | 29.2% |
| 180 mins (3 hrs) | — | 9.19 | 44.5% |
| 1320 mins (22 hrs) | 16.57 | 5.80 | 65.0% |
| 23 days | 18.65 | 2.10 | 88.7% |

Example 16

Formation of a Diammonium Salt Via the Reaction of α-Ketoglutaric Acid (CAS #328-50-7) and N,N-Dimethyldodecylamine (CAS #112-18-5) in a 1:2 Molar Ratio 1.461 g (0.01 moles) of alpha-ketoglutaric acid was dissolved in 6 mL of dry acetone. This solution was added dropwise with stirring over the course of 1-2 minutes to a separate solution of 4.268 g (0.02 moles) of N,N-dimethyldodecylamine in 6 mL of dry acetone. No visible indication of reaction was seen except that the combined solution warmed up to about 35-40° C. The mixture was shaken briefly but vigorously, and cooled in a freezer for 30 minutes. Even when cold, still no precipitation of product occurred, but when the mixture was shaken again, the entire mass almost instantly solidified into a solid, white, waxy substance. This solid was warmed up to 30-35° C. to re-liquefy the product so that entrapped acetone could be removed via a stream of nitrogen followed by treatment in a vacuum oven at room temperature. This gave a white, waxy solid in quantitative yield.

Reduction of POV in Sunflower Oil According to One Aspect Presented Herein Using the Diammonium Salt Formed Via the Reaction of Alpha-Ketoglutaric Acid and N,N-Dimethyldodecylamine (Referred to Herein as AKG-DiMeC12A): 15 mL of sunflower oil that had been stored in a plastic bottle at room temperature for 1 year, but never opened during this storage period, was placed into a 30 mL glass vial, and 0.3062 g of AKG-DiMeC12A was added to it. This salt did not dissolve totally, but gave a hazy, gel-like suspension with the sunflower oil. The mixture was allowed to stand on the benchtop in ambient laboratory light at room temperature, and POV measurements were taken periodically. The results are shown in the table below.

| Time since addition of AKG-DiMeC12A | POV (mmol/L) of untreated oil | POV (mmol/L) of treated oil | % Reduction in POV |
|---|---|---|---|
| 50 minutes | 16.55 | 15.36 | 7.2% |
| 1320 mins (22 hrs) | 16.57 | 12.68 | 23.5% |
| 23 days | 18.65 | 3.05 | 83.6% |

Example 17

Formation of an Ammonium Salt Via the Reaction of Pyruvic Acid (CAS #127-17-3) and N-Methyl Diethanolamine (NMDEA, CAS #105-59-9) in a 1:1 Molar Ratio 2.642 g (0.03 moles) of pyruvic acid was dissolved in 5 mL of dry acetone to give a clear solution. This solution was added dropwise with stirring over the course of 1-2 minutes to a second solution made from 3.575 g (0.03 moles) of NMDEA and 5 mL of dry acetone. The resulting mixture became warm (approximately 35-45° C.) and hazy as the acid solution was added. The milky emulsion was vortexed vigorously for a minute, during which time a second phase had coalesced. The mixture was placed in a freezer for at least 1 hour, causing the bottom phase to increase significantly in viscosity, but not solidify. While still cold, the top layer was easily removed via decantation or pipet, and discarded. Residual acetone was removed from the bottom product layer via a stream of nitrogen followed by treatment in a vacuum oven at room temperature. This gave clear, golden colored, highly viscous oil at room temperature in quantitative yield.

Reduction of POV in Sunflower Oil According to One Aspect Presented Herein Using the Diammonium Salt Formed Via the Reaction of Pyruvic Acid and N-Methyl Diethanolamine (Referred to Herein as PA-NMDEA): 15 mL of sunflower oil that had been stored in a plastic bottle at room temperature for 1 year, but never opened during this storage period, was placed into a 30 mL glass vial, and 0.2988 g of PA-NMDEA was added to it. This salt appeared to dissolve and/or disperse, but the resulting mixture was not totally clear; it had a translucent, colloidal appearance. The mixture was allowed to stand on the benchtop in ambient laboratory light at room temperature, and POV measurements were taken periodically. The results are shown in the table below.

| Time since addition of PA-NMDEA | POV (mmol/L) of untreated oil | POV (mmol/L) of treated oil | % Reduction in POV |
|---|---|---|---|
| 75 minutes | 16.55 | 15.79 | 4.6% |
| 185 minutes | — | 12.34 | 25.4% |
| 1320 mins (22 hrs) | 16.57 | 13.24 | 20.1% |
| 23 days | 18.65 | 11.67 | 37.4% |

Example 18

Reduction of POV in a Model Perfume According to One Aspect Presented Herein Using α-Ketoglutaric Acid α-ketoglutaric acid is a strong acid, wherein a solution of 0.114 g of α-ketoglutaric acid in 10 mL of water had a measured pH of 1.75. Consequently, the amount of the α-ketoglutaric acid in solution in a hydroalcoholic perfume base may have to be limited, to prevent alterations of the organoleptic properties on the perfume raw materials.

A model perfume was made using 90/10 v/v ethanol/water as a solvent, to which, a mixture of orange, grapefruit, and bergamot oils was added. The mixed citrus oil was loaded into the solvent at approximately 19.4% v/v (6 mL oil into 25 mL solvent). Approximately 240 mg (1.2% w/v) of α-ketoglutaric acid was dissolved in 20 mL of the mixed citrus perfume, and a POV measurement was taken the following day. The results are shown in the table below.

| Time in Minutes | POV of Treated Perfume | POV of Untreated Perfume |
|---|---|---|
| 0.0 | 11.99 mmol/L | 11.99 mmol/L |
| 1440 (24 hours) | 0.0 indistinguishable from blank | — |

These data show a complete reduction in the POV of the formulated perfume 24 hours after treatment of the formulated perfume with α-ketoglutaric acid.

Example 19

Reduction of POV in a Model Perfume According to One Aspect Presented Herein Using Oxaloacetic Acid Oxaloacetic acid is known to be unstable in aqueous solutions (see H. A. Krebs, Biochemistry (1942) 36, 303-305), leading to evolution of carbon dioxide and pyruvic acid. Nonetheless, oxaloacetic acid is effective in reducing the POV in solutions that will solubilize it (for example, hydroalcoholic perfumes). However, it is unclear whether the POV reduction occurs via oxaloacetic acid directly, or via liberated pyruvic acid, or both. An analysis of the reaction products (acetic acid versus malonic acid) could distinguish the two pathways, but this was not pursued here.

A model perfume was made using 90/10 v/v ethanol/water as a solvent, to which, a mixture of orange, grapefruit, and bergamot oils was added. The mixed citrus oil was loaded into the solvent at approximately 19.4% v/v (6 mL oil into 25 mL solvent). Approximately 166 mg (0.83% w/v) of oxaloacetic acid was dissolved in 20 mL of the mixed citrus perfume, and POV measurements were taken at the times indicated in the table below.

| Time in Minutes | POV of Treated Perfume | POV of Untreated Perfume |
|---|---|---|
| 0.0 | 9.44 mmol/L | 9.44 mmol/L |
| 27 | 5.90 | — |
| 245 | 1.91 | — |
| 1440 (24 hours) | 0.0 indistinguishable from blank | — |

These data show a complete reduction in the POV of the formulated perfume 24 hours after treatment of the formulated perfume with oxaloacetic acid.

Example 20

Formation of an Ammonium Salt Via the Reaction of Phenylglyoxylic Acid (CAS #611-73-4) and 1-(2-hydroxyethyl)-2-imidazolidinone (HEI, CAS #3699-54-5) in a 1:1 Molar Ratio 3.003 g (0.02 moles) of phenylglyoxylic acid was dissolved in 10 mL of dry acetone to give a clear solution. A separate solution was made from 2.603 g (0.02 moles) of 1-(2-hydroxyethyl)-2-imidazolidinone in 10 mL of dry acetone. Since 1-(2-hydroxyethyl)-2-imidazolidinone was supplied as a 75% w/w solution in water, the actual amount of the 75% reagent used was 3.471 g to compensate for the weight of solvent water. The 1-(2-hydroxyethyl)-2-imidazolidinone amine solution was added dropwise with stirring over the course of 3 minutes to the phenylglyoxylic acid solution; no visible indication of reaction was seen, and no warming was noticeable. The mixture was shaken briefly but vigorously, and cooled in a freezer for 30 minutes. Even when cold, still no precipitation of product occurred, so the acetone solvent was removed via a stream of nitrogen followed by treatment in a vacuum oven at room temperature. This gave clear, pale yellow, highly viscous oil in quantitative yield.

Reduction of POV in Model Perfume According to One Aspect Presented Herein Using the Diammonium Salt Formed Via the Reaction of Phenylglyoxylic Acid and 1 (2 hydroxyethyl)-2-imidazolidinone (Referred to Herein as PhGA-HEI): A model perfume was made using 90/10 v/v ethanol/water as a solvent, and a mixture of lime, orange, grapefruit, and bergamot oils as the perfume oil. The mixed citrus oil was added into the solvent at approximately 16.7% v/v (40 mL oil into 200 mL solvent, 240 mL total perfume). Approximately 150 mg (1.0% w/v) of the PhGA-HEI salt was dissolved in 15 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Days | POV of Treated Perfume | POV of Untreated Perfume |
|---|---|---|
| 0.0 | — | 5.15 mmol/L |
| 1 | 3.51 mmol/L | 6.31 |
| 2 | 3.18 | 6.77 |
| 4 | 3.06 | 7.14 |
| 7 | 2.94 | 7.13 |

The results shown above represents a 58.8% reduction in POV relative to untreated material 7 days after addition of PhGA-HEI. It appears that while the phenylglyoxylic acid moiety does work to lower the POV in the model perfume, it is less reactive/slower than the non-aryl α-oxocarboxylic acids studied. This difference in reactivity may be useful in some circumstances.

Example 21

Formation of a Diammonium Salt Via the Reaction of α-Ketoglutaric Acid (CAS #328-50-7) and 1-(2-hydroxyethyl)-2-imidazolidinone (HEI, CAS #3699-54-5) in a 1:2 Molar Ratio 2.922 g (0.02 moles) of alpha-ketoglutaric acid (AKG) was dissolved in 10 mL of dry acetone to give a clear solution. A separate solution was made from 5.206 g (0.04 moles) of 1-(2-hydroxyethyl)-2-imidazolidinone (HEI) in 10 mL of dry acetone. Since HEI was supplied as a 75% w/w solution in water, the actual amount of the 75% reagent used was 6.942 g to compensate for the weight of solvent water. The HEI amine solution was added dropwise with stirring over the course of 3 minutes to the AKG solution; no visible indication of reaction was seen, and no warming was noticeable. The mixture was shaken briefly but vigorously, and cooled in a freezer for 1 hour. Even when cold, still no precipitation of product occurred, so the acetone solvent was removed via a stream of nitrogen followed by treatment in a vacuum oven at room temperature. This gave clear, water-white, extremely viscous oil in quantitative yield.

Reduction of POV in Model Perfume According to One Aspect Presented Herein Using the Diammonium Salt Formed Via the Reaction of α-Ketoglutaric Acid and 1 (2 hydroxyethyl)-2-imidazolidinone (Referred to Herein as AKG-HEI): A model perfume was made using 90/10 v/v ethanol/water as a solvent, and a mixture of lime, orange, grapefruit, and bergamot oils as the perfume oil. The mixed citrus oil was loaded into the solvent at approximately 16.7% v/v (40 mL oil into 200 mL solvent, 240 mL total perfume). Approximately 150 mg (1.0% w/v) of the AKG-HEI salt was dissolved in 15 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Days | POV of Treated Perfume | POV of Untreated Perfume |
|---|---|---|
| 0.0 | — | 5.15 mmol/L |
| 1 | 1.12 mmol/L | 6.31 |
| 2 | 0.72 | 6.77 |
| 4 | 0.70 | 7.14 |
| 7 | 0.56 | 7.13 |

The results shown above represent a 92.1% reduction in POV relative to untreated material 7 days after addition of AKG-DiHEI.

Example 22

Formation of an Ammonium Salt Via the Reaction of α-Ketoglutaric Acid (CAS #328-50-7) and N,N-Dimethyldodeclyamine (DiMeC12A, CAS #112-18-5) in a 1:1 Molar Ratio (Referred to Herein as AKG-Mono(DiMeC12A))

2.922 g (0.02 moles) of α-ketoglutaric acid was dissolved in 12 mL of dry acetone. This solution was added dropwise with stirring over the course of 1-2 minutes to a separate solution of 4.268 g (0.02 moles) of N, N-dimethyldodecylamine in 6 mL of dry acetone. The mixture was shaken, but no visible indication of reaction was seen except that the combined solution warmed up to about 35-40° C. The mixture remained clear for a few minutes, but when shaken again, the entire mass instantly solidified into a solid white crystalline block. This solid was warmed up to 30-35° C. to re-liquefy the product so that entrapped acetone could be removed via a stream of nitrogen followed by treatment in a vacuum oven at room temperature. This gave a white, waxy solid in quantitative yield.

A model perfume was made using 90/10 v/v ethanol/water as a solvent, and a mixture of orange, grapefruit, and bergamot oils as the perfume oil. The mixed citrus oil was loaded into the solvent at approximately 19.4% v/v (6 mL oil into 25 mL solvent). Approximately 200 mg (1.0% w/v) of the AKG-monoMeC12A salt was dissolved in 20 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Minutes (in Hours) | POV of Treated Perfume | POV of Untreated Perfume |
|---|---|---|
| 0.0 | 11.99 mmol/L | 11.99 mmol/L |
| 30 (0.5) | 7.01 | — |
| 45 (0.75) | 6.97 | — |
| 60 (1.0) | 7.02 | — |
| 180 (3.0) | 4.89 | — |
| 210 (3.5) | 4.54 | — |
| 240 (4.0) | 3.78 | — |
| 270 (4.5) | 3.77 | — |
| 300 (5.0) | 3.05 | — |
| 340 (5.67) | 2.52 | — |
| 1440 (24 hours) | 0.76 | 11.66 |
| 1470 (24.5 hours) | 0.67 | — |
| 1560 (26 hours) | 0.0 indistinguishable from blank | — |

These data represent represents total and complete reduction in the POV, within 26 hours after the addition of AKG-mono(DiMeC12A).

In addition to the treatment done in a model perfume as described above, a similar experiment was done in mixed citrus oil. A sample of mixed citrus oil was made by combining lime, orange, grapefruit, lemon, mandarin, tangerine, and bergamot oils, so that a variety of terpene hydroperoxides would be present in the treated mixture being tested. Approximately 200 mg (1.0% w/v) of the AKG-mono(DiMeC12A) salt was added into 20 mL of the mixed citrus oil, but a substantial portion of it did not dissolve. POV measurements were taken as a function of time after the addition. An untreated mixed citrus oil sample was handled similarly to the treated oil and also tested, because the POV can rise rapidly with handling of the sample (opening the bottle, agitation, etc.). The results are shown in the table below.

| Time in Minutes (in Hours) | POV of Treated Perfume | POV of Untreated Perfume |
|---|---|---|
| 0.0 | 9.45 mmol/L | 9.45 mmol/L |
| 90 (1.5) | 2.09 | — |
| 100 (1.67) | 2.00 | — |
| 120 (2.0) | — | 10.12 |
| 135 (2.25) | 1.63 | — |
| 180 (3.0) | 1.79 | — |
| 1320 (22.0) | 0.96 | 10.56 |
| 1345 (22.42) | 0.91 | — |
| 1620 (27.0) | — | 10.42 |
| 1660 (27.67) | 0.80 | — |
| 1680 (28.0) | 0.60 | — |

These data represent a 94.2% reduction in POV relative to untreated material 28.0 hours after addition of the AKG-mono(DiMeC12A) salt.

Surface Tension Measurements of Aqueous AKG-monoDiMeC12A: In order to evaluate the surfactant properties of AKG-Mono(DiMeC12A), the reduction in surface tension that it causes in aqueous solution versus pure water was measured. The measurement was made on a Kruss DSA100S Tensiometer by the pendant drop method. A 0.14 weight % solution of AKG-Mono(DiMeC12A) in water was used for the measurement. This concentration was chosen so the results could be compared to the literature value for known surfactant sodium dodecyl sulfate (SDS) at 5 mM, which is approximately 0.15 weight %. The results show that AKG-Mono(DiMeC12A) has significant surfactant properties:

Pure water—71.57 mN/m
AKG-monoDiMeC12A—32.93 mN/m

For comparison, SDS at 5 mM concentration (~0.15 weight %, which is very close to the 0.14 weight % used here) at 273K, has an air-water surface tension in the range of 33.5 to 35.5 mN/m depending on the pH (see Hernainz, F. et al, Colloids Surf. A, 2002, 196, 19-24).

Example 23

Formation of an Ammonium Salt Via the Reaction of Indole-3-Pyruvic Acid (I-3-PA, CAS #392-12-1) and N-Methyldiethanolamine (NMDEA, CAS #105-59-9) in a 1:1 Molar Ratio 0.61 g (0.003 moles) of I-3-PA-NMDEA was placed in 4 mL of methanol, but it only partially dissolved. A separate mixture was made of 0.357 g (0.003 moles) of NMDEA in 2 mL of acetone, which formed a clear solution. The amine solution was added in one portion to the indole-3-pyruvic acid and vortexed vigorously for 1 minute. There was some solid that remained undissolved, so the mixture was placed in a 40° C. water bath. As it warmed, all the material dissolved to form a dark orange, clear solution. The mixture was allowed to cool to room temperature, but no precipitate formed. The solution was placed in a freezer for 30 minutes, during which time light pink needle-like crystals had fallen out. The mother liquor was removed with a pipet; it was shown to contain a substantial amount of lower purity material that could be further recovered by blowing down the solvent under a stream of nitrogen to give a deep orange solid. For the purpose of preliminary experiments, the two portions of product were recombined pending the development of a more efficient crystallization procedure. The yield was quantitative.

A model perfume was made using 90/10 v/v ethanol/water as a solvent, and a mixture of orange, grapefruit, and bergamot oils as the perfume oil. The mixed citrus oil was loaded into the solvent at approximately 19.4% v/v (6 mL oil into 25 mL solvent). Approximately 244 mg (1.2% w/v) of the I-3-PA-NMDEA salt was dissolved in 20 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Minutes | POV of Treated Perfume | POV of Untreated Perfume |
|---|---|---|
| 0.0 | 11.09 mmol/L | 11.09 mmol/L |
| 60 | 0.0 indistinguishable from blank | — |

These data represent a rapid reduction in POV relative to untreated material 60 minutes after addition of the I-3-PA-NMDEA salt.

Example 24

Reduction of POV in a Model Perfume According to One Aspect Presented Herein Using a Diammonium Salt Made from α-Ketoglutaric Acid (CAS #328-50-7) and N-Methyl Diethanolamine (NMDEA, CAS #105-59-9) in a 1:2 Molar Ratio Incorporated on a Solid Support It had been observed that a reduction of POV in citrus oils could be produced even with α-oxocarboxylic acid salts that were practically insoluble in the citrus oil being treated. It appeared that this observation held true for both solid salts and liquid salts (which tend to be of high viscosity), although the rate and efficiency of the reduction was not as high as that for soluble salts. It was hypothesized that the surface area of contact between the α-oxocarboxylic acid salt phase and the citrus oil phase was likely a limiting factor, so if true, any method of increasing the contact area should promote a more rapid, facile reaction.

Towards that goal, an attempt was made to spread a thin, highly disperse layer of the diammonium salt formed from α-ketoglutaric acid and two equivalents of N-methyldiethanolamine (AKG-DiNMDEA) onto a chemically inert, high surface area solid support. In this example, a commercially available household scrubbing pad made of extremely thin stainless steel (a Scotch-Brite Scrubby® pad made by 3M Company) was used.

Preparation of an AKG-DiNMDEA Coated Pad: A single pad was cleaned as follows: The pad was placed in a 250 mL glass beaker and covered completely with pentane. The beaker was sonicated for three minutes, the pentane drained, and the procedure repeated with acetone. The acetone was also drained, and the pad dried in a vacuum oven at room temperature for one hour. The pad weighed 19.229 g both before and after the cleaning procedure, so no discernable weight loss was observed as a result of the cleaning.

A solution was made from 3.0 g of AKG-DiNMDEA and 10 mL of fragrance grade ethanol. The pad was loaded by spreading the solution over the stainless steel pad via pipet, and drying the ethanol off under vacuum at room temperature. This was best accomplished with the solution split into about three portions, with a drying step in between each; there was some run-off when attempted in one portion, because the pad could not completely hold that much solution. When all the ethanol was removed, the viscous AKG-DiNMDEA appeared to cling to the pad tightly enough so that the pad could be transferred between containers without loss of the liquid coating.

Treatment of Mixed Citrus Oil: A sample of mixed citrus oil was made by combining lime, orange, grapefruit, and bergamot oils, so that a variety of terpene hydroperoxides would be present in the treated mixture being tested. Into two separate 250 mL glass bottles, 150 mL each of the mixed citrus oil was placed. This allowed for a significant atmospheric headspace to be present in the closed bottles, which would be replenished by fresh atmosphere/oxygen upon every opening of the bottle to withdraw an aliquot for testing. This arrangement was designed to mimic the oxygen exposure resulting from typical handling in production of a drum of citrus oil raw material, and should lead to realistic levels of autoxidation in the contained oils.

The AKG-DiNMDEA coated pad was placed in one of the bottles (the Treated Sample) and totally submerged under the mixed citrus oil therein. In the second bottle, nothing besides the mixed citrus oil was placed (the Untreated Sample). These bottles were allowed to stand on the laboratory bench under ambient temperature and lighting conditions throughout the testing period. Periodically, an aliquot was withdrawn from each bottle for POV testing. Downward flow of the coating off of the pad, as evidenced by the appearance of a puddle of AKG-DiNMDEA collecting at the bottom of the vessel, took several weeks to occur to a noticeable extent. The interphase contact area presumably became lower as this flow progressed, likely reducing the efficiency of the reduction reaction. Nonetheless, significant protection of the treated citrus oil from autoxidation-induced POV increase occurred, as reported below.

Figure 5:
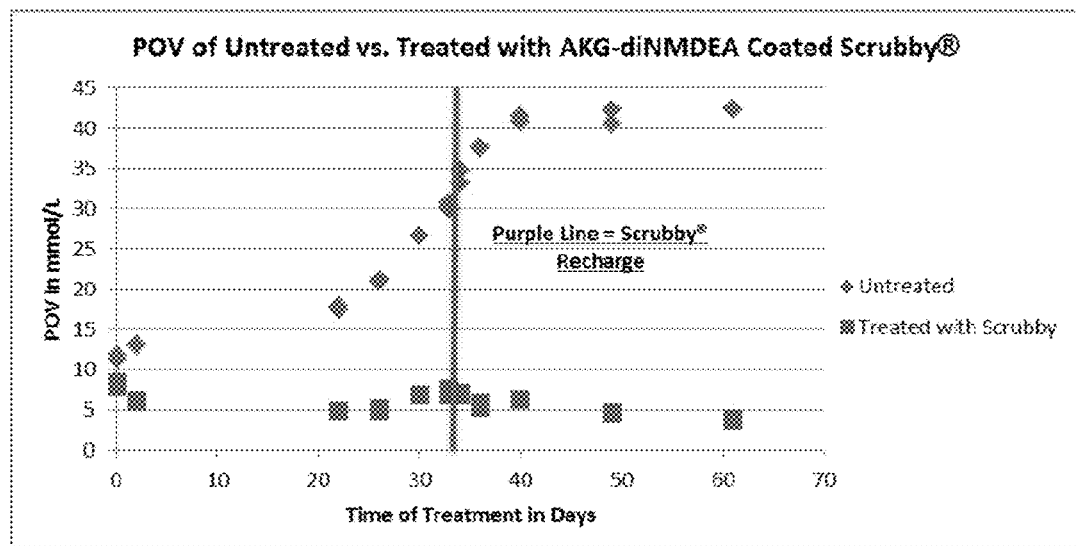
FIG. 5 shows the change in POV of a model perfume treated by a method according to certain aspects presented herein.
Figure 6:
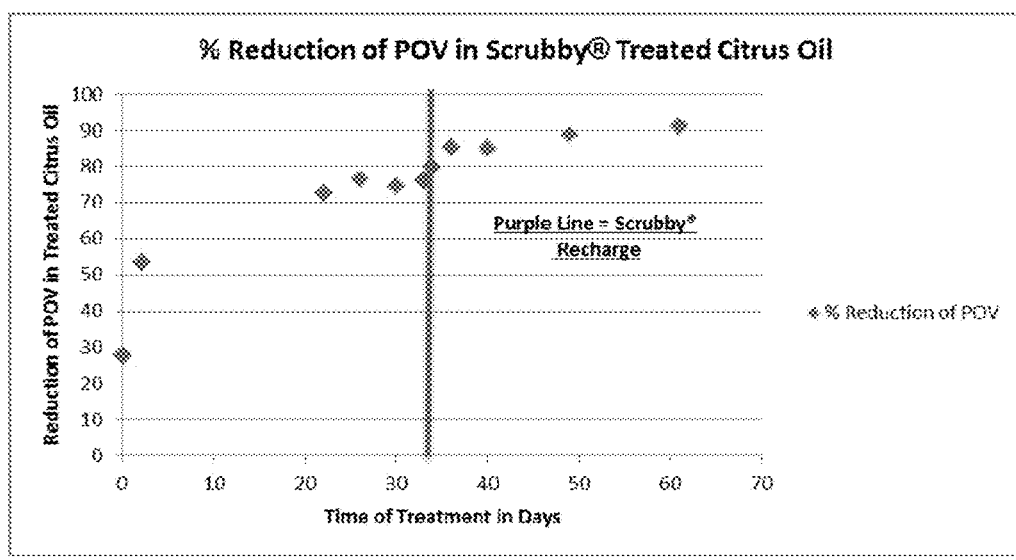
FIG. 6 shows the change in POV of a model perfume treated by a method according to certain aspects presented herein.

Recharge of the Pad: After 26 days, it was observed that the POV of the Treated Sample began to increase slightly (see FIG. 5). Simultaneously, the % POV reduction of Treated Sample relative to Untreated Sample began to decrease slightly (see FIG. 6). This was interpreted to mean that the coated pad had stopped working effectively, perhaps because the AKG-DiNMDEA was chemically spent. Alternatively, perhaps the AKG-DiNMDEA, a viscous liquid, had flowed slowly downward off of the stainless steel coils of the pad. This would create a puddle with low surface area, and therefore the reagent would become ineffective due to insufficient contact with the citrus oil.

The pad was removed from the mixed citrus oil and washed in succession with 100 mL each of acetone, then 95% ethanol, then acetone again. The cleaned pad was dried under vacuum at room temperature, and reloaded with AKG-DiNMDEA. A simpler procedure was tried this time to recharge/reactivate/reload the Scrubby®. Instead of applying a solution and evaporating the solvent, the viscous AKG-DiNMDEA oil was simply rubbed into the steel coils; approximately 3.2 g of AKG-DiNMDEA was placed onto the surface of the steel pad and kneaded in with gloved hands to distribute the oil as evenly as possible. Then the recharged Scrubby® was placed back into the container of treated citrus oil, and POV monitoring was continued as before. The timepoint corresponding to the recharge is shown by a vertical purple line in FIGS. 5 and 6.

Raw POV Titration Data:

| Time since Scrubby Recharge (in Days) | Time in Days | Untreated | Treated with Scrubby |
|---|---|---|---|
| | 0.125 | 11.68 | 8.53 |
| | 0.125 | 11.14 | 7.94 |
| | 2.1 | 12.89 | 5.99 |
| | 2.1 | 13.03 | 6.12 |
| | 22 | 17.37 | 4.91 |
| | 22 | 17.84 | 4.8 |
| | 26 | 21.3 | 5.14 |
| | 26 | 21.02 | 4.9 |
| | 30 | 26.73 | 6.83 |
| | 30 | 26.71 | 6.83 |
| | 33 | 30.73 | 6.86 |
| | 33 | 29.96 | 7.7 |
| | 33 | 30.35 | 7.24 |
| 0.8 | 34 | 34.72 | 6.88 |
| 0.8 | 34 | 33.21 | 6.97 |
| 2.8 | 36 | 37.59 | 5.32 |
| 2.8 | 36 | 37.7 | 5.94 |
| 7 | 40 | 41.47 | 6.29 |
| 7 | 40 | 40.83 | 6.29 |
| 16 | 49 | 42.35 | 4.62 |
| 16 | 49 | 40.51 | 4.58 |
| 28 | 61 | 42.28 | 3.89 |
| 28 | 61 | 42.44 | 3.72 |

| Time since Scrubby Recharge (in Days) | Time in Days | % Reduction of POV |
|---|---|---|
| | 0.125 | 27.8 |
| | 2.1 | 53.2 |
| | 22 | 72.4 |
| | 26 | 76.3 |
| | 30 | 74.4 |
| | 33 | 76 |
| 0.8 | 34 | 79.6 |
| 2.8 | 36 | 85.1 |
| 7 | 40 | 84.7 |
| 16 | 49 | 88.9 |
| 28 | 61 | 91 |

Example 25

Reduction of POV in a Selection of Consumer Products According to One Aspect Presented Herein This Example reports the treatment of exemplary consumer product formulations. The consumer product formulations had a measurable level of oxidation as received, as shown in the table below, but the POV levels were low except the all-purpose cleaner. All of the samples had not been fragranced, so the POV was be associated with autooxidized base components. The five consumer product formulations were spiked with an extremely oxidized limonene that was produced in a photoreactor as a source of mixed limonene hydroperoxide isomers (the POV was 1434 mmol/L). The oxidized limonene was spiked into each at a level of 10 µL per gram, so approximately 14.3 mmol/L of POV would be added to the existing, as-received POV.

In all cases, the treatment with an α-oxocarboxylic acid ammonium salt produced a rapid and extensive lowering of the sample's POV; the hydroperoxides present in the sample were consumed/destroyed via a defined, controlled reaction with the α-oxocarboxylic acid to yield harmless and predictable by-products. In some cases, the untreated sample showed a much slower but steady reduction in POV; this is likely due to the limonene hydroperoxides reacting with and oxidizing base components, to form unknown by-products. This may have deleterious effects on the formulation in many cases, such as malodor formation, discoloration, changes in physical properties, etc. Such uncontrolled, undirected lowering of POV will likely lower the skin sensitizing potential of a sample due to consumption of sensitizing hydroperoxides, but is not necessarily positive to the formulation in all aspects.

POV of Consumer Product Samples as Received (Before Spike with Oxidized Limonene)

| Consumer Products | POV (mmol/L) | Amount of Sample Titrated | Notes |
|---|---|---|---|
| #1. Hand Dishwashing Liquid | 2.65 | 1 mL | 1.0083 g, Viscous white liquid |
| #2. Shampoo | 0.97 | 1 mL | 0.9992 g, Viscous white liquid |
| #3. All Purpose Spray Cleaner | 7.30 | 1 mL | 0.9910 g, Mobile colorless liquid |
| #4. Skin Cream | 0 | 1.0332 g | Thick white cream |
| #5. Antiperspirant Stick | 1.65 | 1.0766 g | White semi-solid |

Sample Preparation: 40 mL (Sample #3) or 40 g (Samples #1, 2, 4 & 5) were each spiked with 0.4 mL of oxidized limonene and mixed until homogeneous. Half of each spiked consumer product sample was transferred to a second container, and treated as described in the table below with 0.5-1% (w/w) of a 2-oxocarboxylic acid ammonium salt, then mixed to homogeneity. Each of the five pairs of two samples, treated & un-treated, were allowed to stand on the benchtop in ambient laboratory light at room temperature, and POV measurements were taken periodically. The results are described below.

| Spiked Consumer Product | 2-Oxocarboxylic Acid Ammonium Salt Used for Treatment (dosage and identification) |
|---|---|
| #1. Hand Dishwashing Liquid Soap | 0.5% (w/w) of PA-NMDEA:pyruvic acid + N-methyl diethanolamine, 1:1 molar ratio |
| #2. Shampoo | 0.5% (w/w) of PA-NMDEA:pyruvic acid + N-methyl diethanolamine, 1:1 molar ratio |
| #3. All Purpose Spray Cleaner | 1% (w/w) of AKG-DiNMDEA:α-ketoglutaric acid + N-methyldiethanolamine, 1:2 molar ratio |
| #4. Skin Cream | 1% (w/w) of AKG-DiMeC12A:α-ketoglutaric acid + N,N-dimethyldodecylamine, 1:2 molar ratio |
| #5. Anti-Perspirant Stick | 1% (w/w) of AKG-diTMEEA:α-ketoglutaric acid + Tris[2-(2-(methoxyethoxy)ethyl]amine, 1:2 molar ratio |

Figure 7:
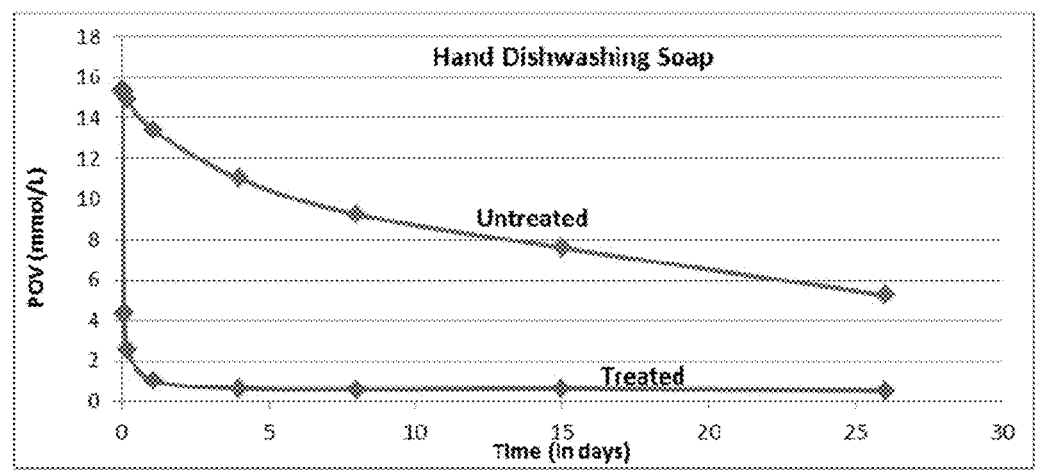
FIG. 7 shows the POV of a liquid soap formulation treated by a method according to certain aspects presented herein.
Figure 8:
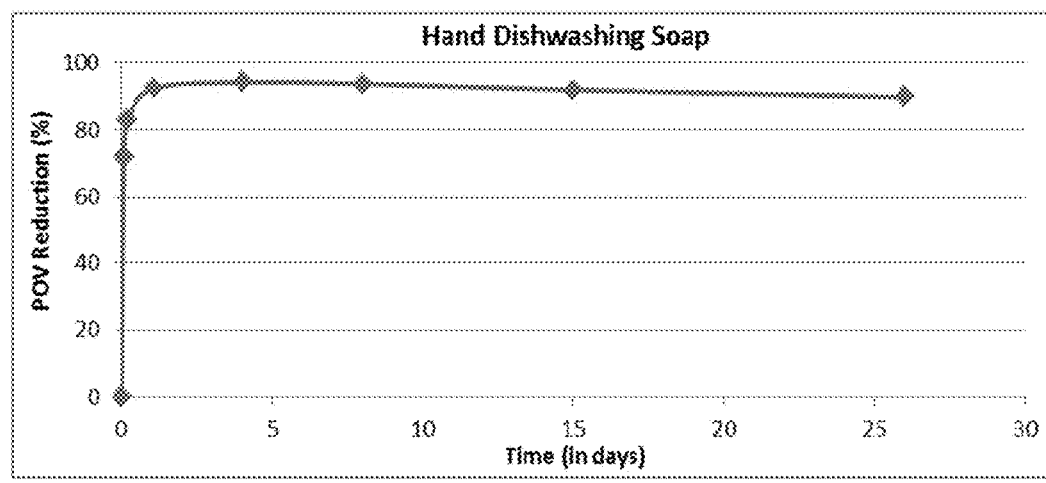
FIG. 8 shows the percent reduction in POV of a liquid soap formulation treated by a method according to certain aspects presented herein.

Sample 1, Hand Dishwashing Liquid Soap (HDLS)—See FIGS. 7 and 8:

| Time since addition of PA-NMDEA | POV (mmol/L) of untreated HDLS | POV (mmol/L) of treated HDLS | % Reduction in POV |
|---|---|---|---|
| 110 minutes | 15.38 | 4.33 | 71.8% |
| 280 minutes (4.67 h) | 14.89 | 2.54 | 82.9% |
| 26 hrs | 13.4 | 1.03 | 92.3% |
| 4 days | 11.01 | 0.65 | 94.1% |
| 8 days | 9.25 | 0.59 | 93.6% |
| 15 days | 7.6 | 0.62 | 91.8% |
| 26 days | 5.23 | 0.54 | 89.7% |

Figure 9:
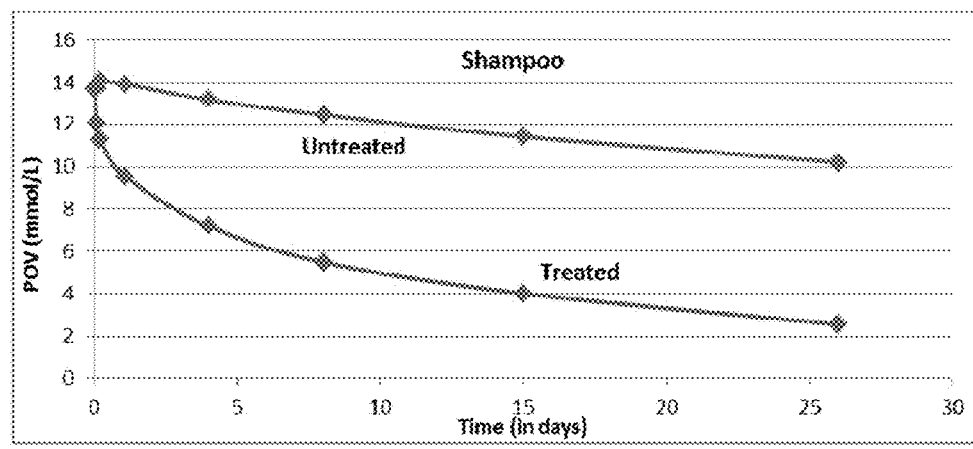
FIG. 9 shows the POV of a shampoo formulation treated by a method according to certain aspects presented herein.
Figure 10:
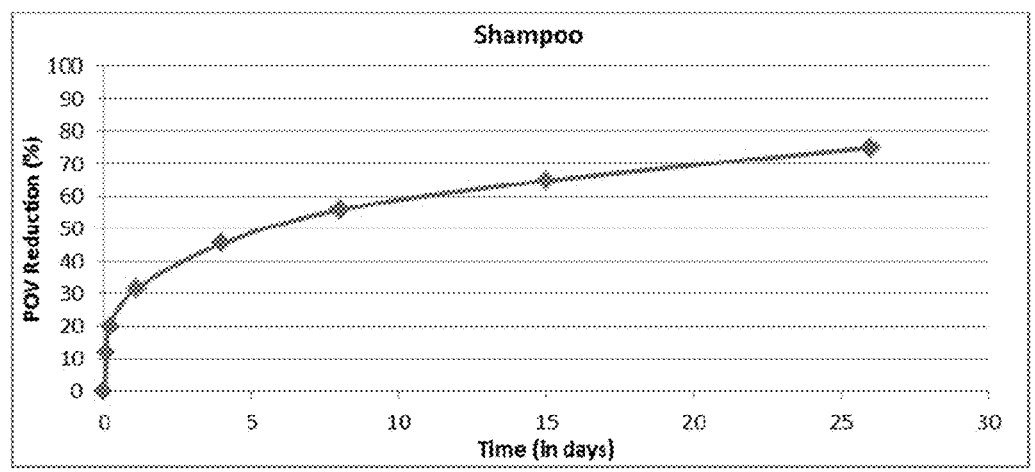
FIG. 10 shows the percent reduction in POV of a shampoo formulation treated by a method according to certain aspects presented herein.

Sample 2, Shampoo—See FIGS. 9 and 10:

| Time since addition of PA-NMDEA | POV (mmol/L) of untreated Shampoo | POV (mmol/L) of treated Shampoo | % Reduction in POV |
|---|---|---|---|
| 120 minutes | 13.69 | 12.04 | 12.1% |
| 280 minutes (4.67 h) | 14.05 | 11.25 | 19.9% |
| 26 hrs | 13.91 | 9.53 | 31.5% |
| 4 days | 13.15 | 7.18 | 45.4% |
| 8 days | 12.43 | 5.48 | 55.9% |
| 15 days | 11.41 | 4.01 | 64.9% |
| 26 days | 10.2 | 2.55 | 75.0% |

Figure 11:
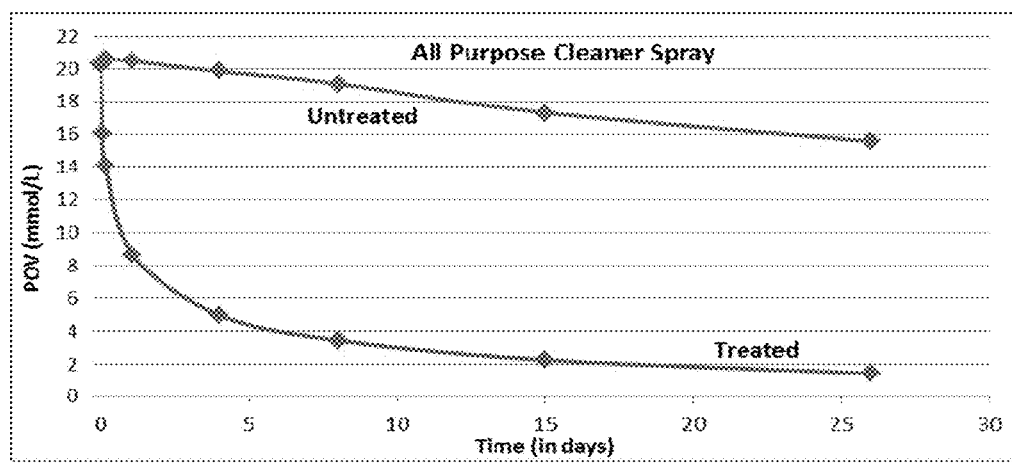
FIG. 11 shows the POV of an all-purpose cleaner spray formulation treated by a method according to certain aspects presented herein.
Figure 12:
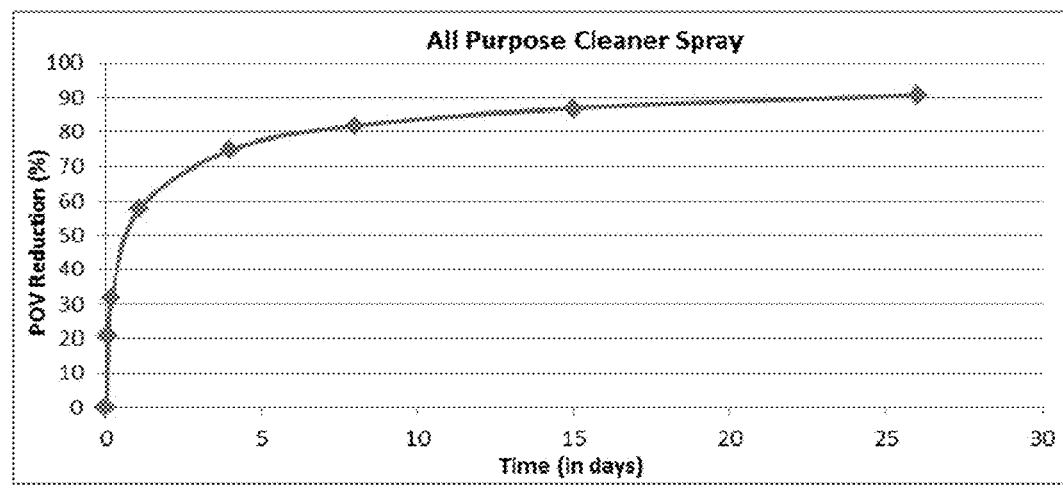
FIG. 12 shows the percent reduction in POV of an all-purpose cleaner spray formulation treated by a method according to certain aspects presented herein.

Sample 3, All Purpose Cleaner (APC)—See FIGS. 11 and 12:

| Time since addition of AKG-DiNMDEA | POV (mmol/L) of untreated APC | POV (mmol/L) of treated APC | % Reduction in POV |
|---|---|---|---|
| 100 minutes | 20.28 | 16.07 | 20.8% |
| 260 minutes (4.33 h) | 20.62 | 14.1 | 31.6% |
| 26 hrs | 20.47 | 8.67 | 57.6% |
| 4 days | 19.84 | 4.99 | 74.8% |
| 8 days | 19.08 | 3.46 | 81.9% |
| 15 days | 17.32 | 2.27 | 86.9% |
| 26 days | 15.57 | 1.44 | 90.8% |

Figure 13:
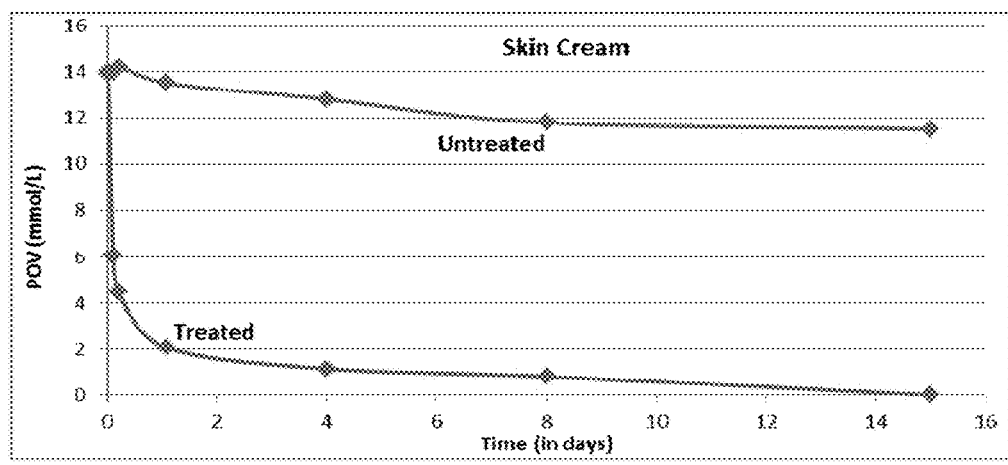
FIG. 13 shows the POV of a skin cream formulation treated by a method according to certain aspects presented herein.
Figure 14:
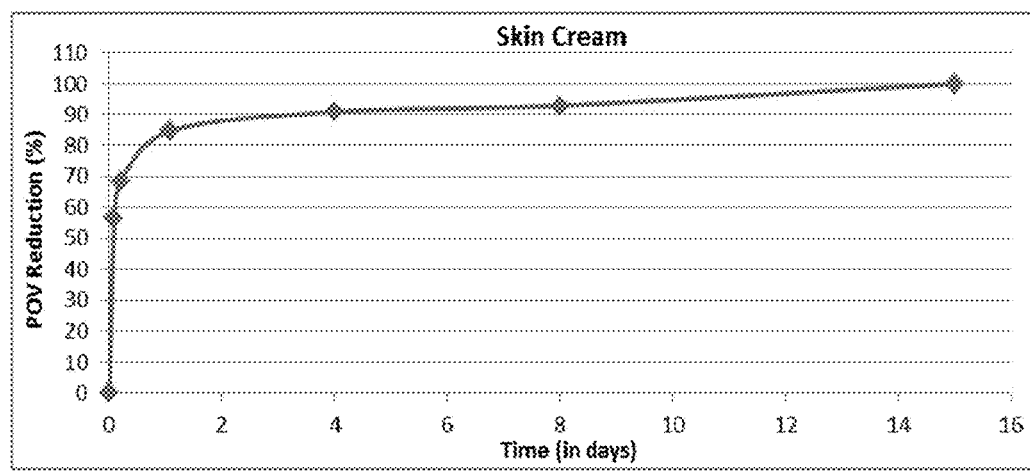
FIG. 14 shows the percent reduction in POV of a skin cream formulation treated by a method according to certain aspects presented herein.

Sample 4, Skin Cream—See FIGS. 13 and 14:

| Time since addition of AKG-DiMeC12A | POV (mmol/L) of untreated Skin Cream | POV (mmol/L) of treated Skin Cream | % Reduction in POV |
|---|---|---|---|
| 140 minutes | 13.99 | 6.06 | 56.7% |
| 300 minutes (5 h) | 14.23 | 4.5 | 68.4% |
| 26 hrs | 13.52 | 2.08 | 84.6% |
| 4 days | 12.8 | 1.16 | 90.9% |
| 8 days | 11.79 | 0.82 | 93.0% |
| 15 days | 11.51 | 0 | 100.0% |

Figure 15:
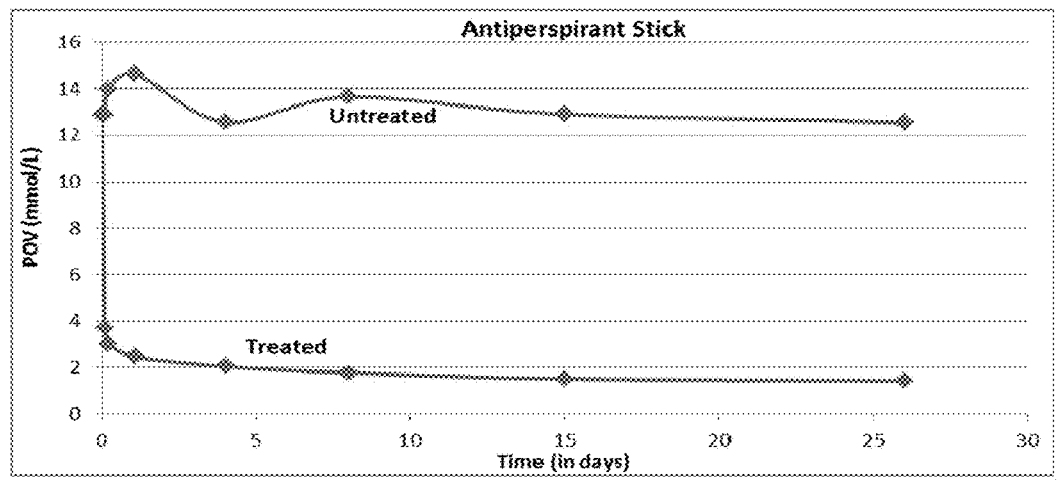
FIG. 15 shows the POV of an anti-perspirant stick formulation treated by a method according to certain aspects presented herein.
Figure 16:
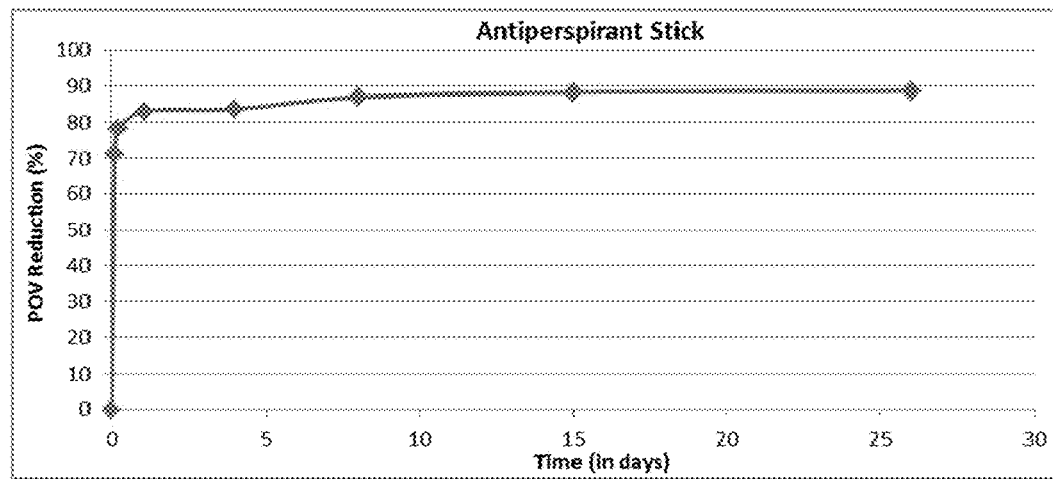
FIG. 16 shows the percent reduction in POV of an anti-perspirant stick formulation treated by a method according to certain aspects presented herein.

Sample 5, Antiperspirant Stick (APS)—See FIGS. 15 and 16:

| Time since addition of AKG-DiTMEEA | POV (mmol/L) of untreated APS | POV (mmol/L) of treated APS | % Reduction in POV |
|---|---|---|---|
| 150 minutes | 12.87 | 3.7 | 71.3% |
| 310 minutes (5.17 h) | 13.97 | 3.03 | 78.3% |
| 26 hrs | 14.64 | 2.46 | 83.2% |
| 4 days | 12.57 | 2.04 | 83.8% |
| 8 days | 13.65 | 1.77 | 87.0% |
| 8 days* | 13.46 | 1.8 | 86.6% |
| 15 days | 12.9 | 1.50 | 88.4% |
| 26 days | 12.55 | 1.42 | 88.7% |

Example 26

Reduction of POV in a Selection of Essential Oils Obtained from Non-Citrus Sources According to One Aspect Presented Herein In this Example, a series of non-citrus-derived essential oils were treated as described below with AKG-DiTMEEA (the diammonium salt made from alpha-ketoglutaric acid (AKG, CAS #328-50-7) and Tris[2-(2-(methoxyethoxy)ethyl]amine (TMEEA, CAS #70384-51-9) in a 1:2 molar ratio). The results indicate that the claimed treatment is effective over a broad range of essential oils, which contain a broad range of terpenes and other small organic molecules such as aromatics. Therefore a very broad range of organic hydroperoxides will be present as autoxidation products in these other oil types, and they all appear to be reduced by 2-oxoacids (specifically an α-ketoglutarate ammonium salt in this case).

The data below shows nine oils along with the POV obtained on each as received from production stock. For each oil, 20 mL was placed in separate 30 mL glass vials, and subjected to the following procedure for 8 days on a daily basis; the vial was opened to refresh the atmospheric headspace, then reclosed and shaken to maximize the gas/liquid contact, then stored on the benchtop under ambient laboratory temperature and lighting conditions. This procedure was designed to mimic the typical handling of a container in a production setting, in which the oil gets consumed in many small aliquots, rather than an entire container at a time.

On Day 4, each oil sample was split in half, so two 10 mL aliquots were placed in separate vials to create a "Treated" and an "Untreated" sample. To the Treated sample of each oil type, AKG-DiTMEEA was added as per the Dosing chart below. The pine oil had an extremely high POV, so the dosing and measurement protocol was somewhat different from the other oils. The daily opening, shaking, and standing procedure continued for another four days until the POV measurements were taken. It can be seen that 8 days of such handling of the untreated oils caused significant increases in POV measurement.

The Siberian Pine Oil, even as received, had a POV that was unusually high, to such a degree that stoichiometric depletion of the AKG-DiTMEEA is likely to occur. For this reason, two levels of AKG-DiTMEEA treatment were tried, ×2 and ×4 the treatment used on the other oils. The results indicate that even greater amounts may be necessary to completely remediate this Pine Oil sample, because AKG-DiTMEEA has a high molecular weight due to the large amine groups, and there is a low stoichiometric ability to scavenge hydroperoxides per unit weight. A different, lower molecular weight 2-oxoacid salt may be a better choice.

POV of Untreated Oils, Before and after Handling:

| | POV (mmol/L) of untreated oils | |
|---|---|---|
| Essential oils | As Received (Day 0) | After Handling (Day 8) |
| #1: Basil oil | 10.56 | 23.88 |
| #2: Coriander oil | 13.23 | 23.60 |
| #3: Patchouli oil | 2.42 | 4.89 |
| #4: Star Anise oil | 1.44 | 3.52 |
| #5: Cinnamon leaf oil | 2.60 | 4.51 |
| #6: Cedarwood oil Virginian | 8.87 | 15.00 |

-continued

| | POV (mmol/L) of untreated oils | |
|---|---|---|
| Essential oils | As Received (Day 0) | After Handling (Day 8) |
| #7: Pine oil Siberian | 43.93 | 48.08 |
| #8: Lavender oil | 14.94 | 24.59 |
| #9: Petitgrain oil | 10.24 | 21.23 |

Dosing/Treatment of Non-Citrus Essential Oils with AKG-DiTMEEA

| | | Treated | | |
|---|---|---|---|---|
| Essential oils | Untreated Total Volume | Total Volume | Added AKG TMEEA disalt | Appearance of Treated Compared to Untreated Sample |
| #1: Basil oil | 10 mL | 10 mL | 0.2 mL | Slight haziness, no color change |
| #2: Coriander oil | 10 mL | 10 mL | 0.2 mL | Clear, from colorless to slightly yellow |
| #3: Patchouli oil | 10 mL | 10 mL | 0.2 mL | Slight haziness, no color change |
| #4: Star Anise oil | 10 mL | 10 mL | 0.2 mL | Slight haziness, no color change |
| #5: Cinnamon leaf oil | 10 mL | 10 mL | 0.2 mL | Clear, no color change |
| #6: Cedarwood oil, Virginian | 10 mL | 10 mL | 0.2 mL | Slight haziness, from colorless to slightly yellow |
| #7: Pine oil, Siberian | 5 mL | 5 mL | 0.2 mL | Clear, from colorless to slightly yellow |
| | | 5 mL | 0.4 mL | Clear, from colorless to slightly yellow |
| #8: Lavender oil | 10 mL | 10 mL | 0.2 mL | Clear, from colorless to slightly yellow |
| #9: Petitgrain oil | 10 mL | 10 mL | 0.2 mL | Clear, same color |

AKG-DiTMEEA Treatment (4 Days) of Non-Citrus Essential Oils

| Oil Type | POV (mmol/L) of Untreated Oil | POV (mmol/L) of Treated Oil | % Reduction in POV |
|---|---|---|---|
| Basil Oil | 23.88 | 2.49 | 89.6 |
| Coriander Oil | 23.60 | 2.44 | 89.7 |
| Patchouli Oil | 4.89 | 0.00 | 100.0 |
| Star Anise Oil | 3.52 | 0.38 | 89.2 |
| Cinnamon Leaf Oil | 4.51 | 0.57 | 87.5 |
| Cedarwood Oil, Virginian | 15.00 | 0.72 | 95.2 |
| Pine Oil, Siberian (x2 Treatment Level) | 48.08 | 24.8 | 48.4 |
| Pine Oil, Siberian (x4 Treatment Level) | 48.08 | 15.21 | 68.4 |
| Lavender Oil | 24.59 | 5.83 | 76.3 |
| Petitgrain Oil | 21.23 | 4.28 | 79.9 |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method, wherein the method reduces the peroxide value (POV) of a perfume, body care product, cosmetic product, homecare product, perfumery raw material, flavored article, or food raw material, the method comprising:
   a. adding an α-oxocarboxylic acid to the perfume, body care product, cosmetic product, homecare product, perfumery raw material, flavored article, or food raw material having a first POV level;
   b. mixing the α-oxocarboxylic acid into the perfume, body care product, cosmetic product, homecare product, perfumery raw material, flavored article, or food raw material for a time sufficient to reduce the first POV level to a pre-determined second lower level; and
   c. removing the α-oxocarboxylic acid from the formulated perfume, body care product, cosmetic product, homecare product, perfumery raw material, flavored article, or food raw material having the pre-determined second lower level.

2. The method of claim 1, wherein the step of removing the α-oxocarboxylic acid from the formulated perfume, body care product, cosmetic product, homecare product, perfumery raw material, flavored article, or food raw material comprises a liquid-liquid extraction.

3. The method of claim 1, further comprising treating the formulated perfume, body care product, cosmetic product, homecare product, perfumery raw material, flavored article, or food raw material with a carbonate salt after removing the α-oxocarboxylic acid to reduce the acidity of the formulated perfume, body care product, perfumery raw material, flavored article, or food raw material.

* * * * *